US010959993B2

(12) United States Patent
Merchant et al.

(10) Patent No.: US 10,959,993 B2
(45) Date of Patent: Mar. 30, 2021

(54) COMBINATION OF BCL-2 INHIBITOR AND MEK INHIBITOR FOR THE TREATMENT OF CANCER

(71) Applicants: Genentech, Inc., South San Francisco, CA (US); Board of Regents, The University of Texas System, Austin, TX (US)

(72) Inventors: Mark Merchant, South San Francisco, CA (US); Deepak Sampath, South San Francisco, CA (US); Marina Konopleva, Houston, TX (US); Lina Han, Houston, TX (US)

(73) Assignee: Genentech, Inc., North San Francisco, CA (US)

( * ) Notice: Subject to any disclaimer, the term of this patent is extended or adjusted under 35 U.S.C. 154(b) by 0 days.

(21) Appl. No.: 15/767,914

(22) PCT Filed: Nov. 3, 2016

(86) PCT No.: PCT/US2016/060271
§ 371 (c)(1),
(2) Date: Apr. 12, 2018

(87) PCT Pub. No.: WO2017/079399
PCT Pub. Date: May 11, 2017

(65) Prior Publication Data
US 2018/0303815 A1    Oct. 25, 2018

Related U.S. Application Data

(60) Provisional application No. 62/263,082, filed on Dec. 4, 2015, provisional application No. 62/250,231, filed on Nov. 3, 2015.

(51) Int. Cl.
*A61K 31/5365*    (2006.01)
*A61K 31/497*    (2006.01)
(Continued)

(52) U.S. Cl.
CPC ........ *A61K 31/4523* (2013.01); *A61K 31/496* (2013.01); *A61K 45/06* (2013.01); *A61P 35/02* (2018.01); *A61K 2300/00* (2013.01)

(58) Field of Classification Search
CPC .......................... A61K 31/4523; A61K 31/496
(Continued)

(56) References Cited

U.S. PATENT DOCUMENTS 7,803,839 B2    9/2010  Aay et al.
2010/0009934 A1*  1/2010  Rickles .................. A61K 31/00
514/64

(Continued)

FOREIGN PATENT DOCUMENTS

WO    2014027056 A1    2/2014
WO    2015051252 A1    4/2015

OTHER PUBLICATIONS

Hoeflich et al. "Intermittent Administration of MEK Inhibitor GDC-0973 plus PI3K Inhibitor GDC-0941 Triggers Robust Apoptosis and Tumor Growth Inhibition", Can Res, 2011, vol. 72, issue 1, pp. 210-219. (Year: 2011).*

(Continued)

*Primary Examiner* — Shengjun Wang
(74) *Attorney, Agent, or Firm* — Armstrong Teasdale LLP

(57) ABSTRACT

The present invention is directed to a combination therapy involving a selective Bcl-2 inhibitor and a MEK inhibitor for the treatment of a patient in need of such a therapy. The patient in need of the combination therapy is suffering from cancer, such as acute myeloid leukemia.

12 Claims, 18 Drawing Sheets

(51) Int. Cl.
  *A61K 31/4523* (2006.01)
  *A61K 45/06* (2006.01)
  *A61K 31/496* (2006.01)
  *A61P 35/02* (2006.01)
(58) Field of Classification Search
  USPC ...................................... 514/210.18, 253.04
  See application file for complete search history.

(56) References Cited

U.S. PATENT DOCUMENTS

| 2010/0305122 | A1 | 12/2010 | Bruncko et al. | |
|---|---|---|---|---|
| 2011/0129456 | A1* | 6/2011 | Wang ................ | A61K 31/4745 424/131.1 |
| 2012/0129853 | A1 | 5/2012 | Elmore et al. | |
| 2012/0157470 | A1 | 6/2012 | Catron et al. | |
| 2014/0248262 | A1 | 9/2014 | Sampath et al. | |

OTHER PUBLICATIONS

Souers et al. "ABT-199, a potent and selective BCL-2 inhibitor, achieves antitumor activity while sparing platelets", Nature Medicine, 2013, vol. 19, No. 2, pp. 202-210. (Year: 2013).*
Grazia et al. "Toward combinatorial targeted therapy in melanoma: From pre-clinical evidence to clinical application (review)" International J. Oncology, 2014, vol. 45, pp. 929-949 (Year: 2014).*
Gocek et al., "The Potential of Vitamin D-Regulated Intracellular Signaling Pathways as Targets for Myeloid Leukemia Therapy", J Clin Med., Apr. 2015, vol. 4, No. 4, pp. 504-534.
Han et al., "Concomitantly Targeting BCL-2 with Venetoclax (ABT-199/GDC-0199) and MAPK Signaling with Cobimetinib (GDC-0973) in Acute Myeloid Leukemia Models", Blood, Dec. 3, 2015, vol. 126, No. 23, 5 pages.
Konopleva et al., "MEK Inhibition Enhances ABT-737-Induced Leukemia Cell Apoptosis via Prevention of ERK activated MCL-1 induction and Modulation of MCL-1/BIM Complex", Leukemia, Apr. 2012, vol. 26, No. 4, pp. 778-787.
Lee et al., "Tumor Progression Locus 2 (Tpl2) Kinase as a Novel Therapeutic Target for Cancer: Double-Sided Effects of Tpl2 on Cancer", Int J. Mol. Sci., 2015, vol. 16, pp. 4471-4491.
Milella et al., "Synergistic induction of apoptosis by simultaneous disruption of the Bcl-2 and MED/MAPK pathways in acute myelogenous leukemia", Blood, May 1, 2002, vol. 99, No. 9, pp. 3461-3464.
Pan et al., "Selective BCL-2 Inhibition by ABT-199 Causes On-Target Cell Death in Acute Myeloid Leukemia", Cancer Discovery, Mar. 2014, pp. 362-375.
Ricciardi et al., "Preclinical Approach to Sensitize Multiple Myeloma Cells: Combination of the MEK Inhibitor PD0325901 with ABT-737 or Mevinolin", Blood, Nov. 20, 2009, vol. 114, No. 22, p. 731.
Tan et al., "Bcl-2/Bcl-xL Inhibition Increases the Efficacy of MEK Inhibition Alone and in Combination with PI3 Kinase Inhibition in Lung and Pancreatic Tumor Models", Molecular Cancer Therapeutics, Jun. 2013, vol. 12, No. 6, pp. 853-864.
International Search Report and Written Opinion for PCT/US2016/060271, dated Mar. 3, 2017, 14 pages.
Ricciardi et al., "Pro-Apoptotic Synergistic Interactions between ERK1/2 and Bcl-2 Inhibitors in Acute Myeloid Leukemia Cells", Blood, 2004, vol. 104, No. 11, Abstract 3400, 2 pages.
Zhang et al., "Synergistic induction of apoptotic cell death in AML by targeting Bcl-2 with ABT-199 in combination with Bcl-Xl/Mcl-1 inhibition or selective kinase inhibitors", Clinical Lymphoma, Myeloma & Leukemia, Sep. 2015, Abstract No. 218, 1 page.
Office Action dated Aug. 6, 2019 in counterpart Japanese Application No. 2018-522692, 8 pages.
Akinleye et al., "MEK and the inhibitors: from bench to bedside", Journal of Hematology & Oncology, 2013, vol. 6, No. 27, 11 pages.
Barrett et al., "The discovery of the benzhydroxamate MEK inhibitors CI-1040 and PD 0325901", Bioorganic & Medicinal Chemistry Letters, 2018, vol. 18, pp. 6501-6504.
Chernigovskaya et al., "Effects of selective Bcl-2 inhibitor HA14-1 treatments on functional activity of magnocellular vasopressinergic neurons of rat hypothalamus", Neuroscience Letters, 2008, vol. 437, pp. 59-64.
Frémin et al., "From basic research to clinical development of MED1/2 inhibitors for cancer therapy", Journal of Hematology & Oncology, 2010, vol. 3, No. 8, 11 pages.
Gandi et al., "Phase I Study of Navitoclax (ABT-263), a Novel Bcl-2 Family Inhibitor, in Patients With Small-Cell Lung Cancer and Other Solid Tumors", Journal of Clinical Oncology, Mar. 1, 2011, vol. 29, No. 7, pp. 909-916.
Gautschi et al., "Activity of a Novel bcl-2-xL-Bispecific Antisense Oligonucleotide Against Tumors of Diverse Histologic Origins", Journal of the National Cancer Institute, Mar. 21, 2001, vol. 93, No. 6, pp. 463-471.
Van Delft et al., "The BH3 mimetic ABT-737 t, argets selective Bcl-2 proteins and efficiently induces apoptosis via Bak/Bax if Mcl-1 is neutralized", Cancer Cell, Nov. 2006, vol. 10, pp. 389-399.
Vogler, M., "Targeting BCL2-Proteins for the Treatment of Solid Tumours", Advances in Medicine, 2014, vol. 2014, Article ID 943648, 14 pages.
Wang et al., "Clinical experience of MEK inhibitors in cancer therapy", Biochimica et Biophysica Acta, 2007, vol. 1773, pp. 1248-1255.
Wu et al., "MEK1/2 Inhibitors: Molecular Activity and Resistance Mechanisms", Semin Oncol., Dec. 2015, vol. 42, No. 6, pp. 849-862.

* cited by examiner

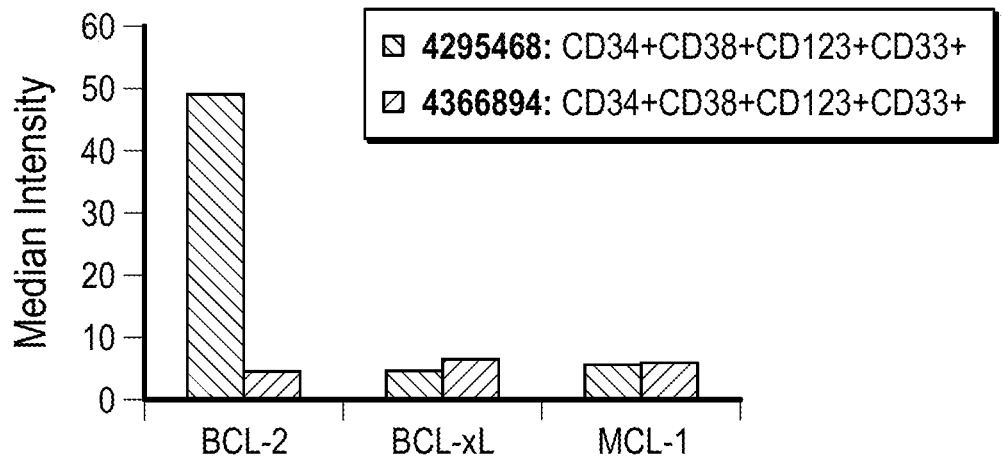
FIG. 4B
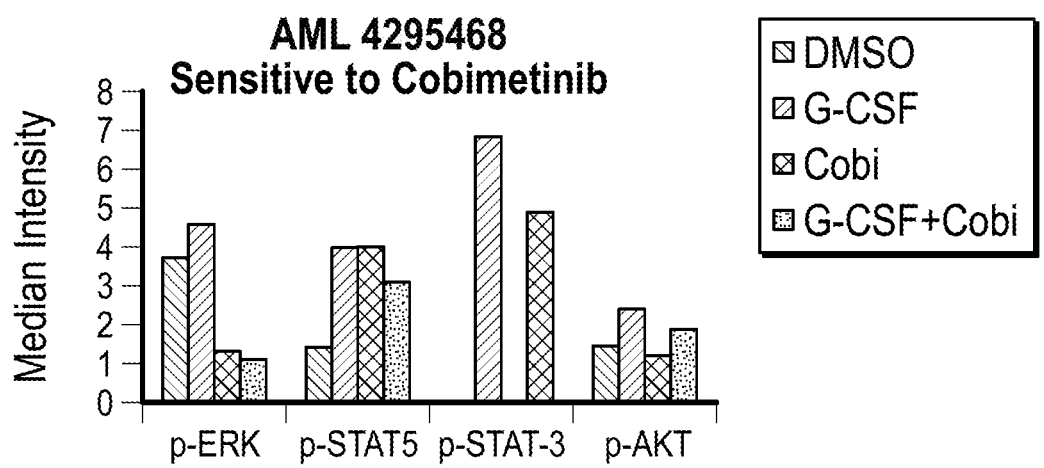
FIG. 4C
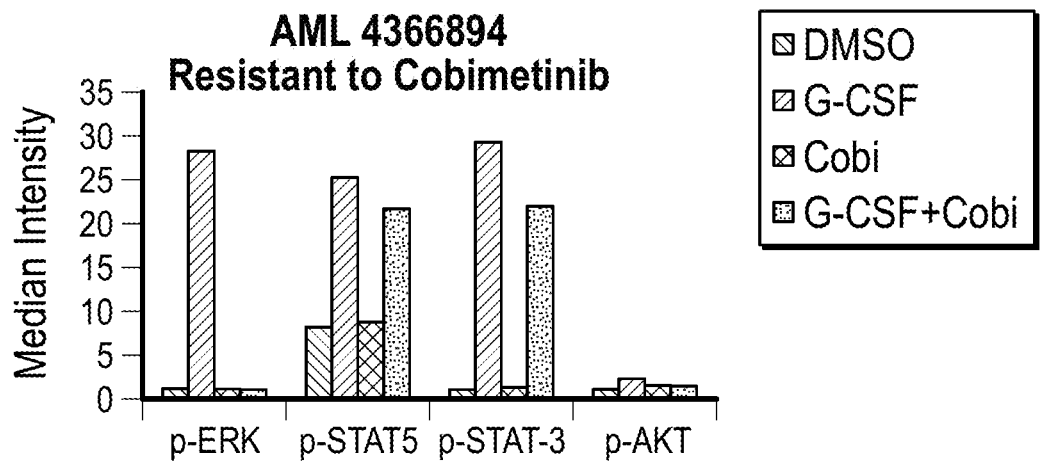

COMBINATION OF BCL-2 INHIBITOR AND MEK INHIBITOR FOR THE TREATMENT OF CANCER

CROSS REFERENCE TO RELATED APPLICATIONS

This application is the 35 U.S.C. § 371 national stage of International Application No. PCT/US2016/060271, filed Nov. 3, 2016, the contents of which are hereby incorporated by reference as if set forth in its entirety. International Application No. PCT/US2016/060271 claims priority to U.S. provisional application Ser. No. 62/250,231, filed Nov. 3, 2015, the contents of which are hereby incorporated by reference as if set forth in its entirety. International Application No. PCT/US2016/060271 claims priority to U.S. provisional application Ser. No. 62/263,082, filed Dec. 4, 2015, the contents of which are hereby incorporated by reference as if set forth in its entirety.

FIELD OF THE INVENTION

The present invention is directed to a combination therapy involving a selective Bcl-2 inhibitor and a MEK inhibitor for the treatment of a patient in need of such a therapy, and more particularly is directed to the combination of venetoclax (ABT-199/GDC-0199) and cobimetinib (GDC-0973).

BACKGROUND OF THE INVENTION

Protein kinases are enzymes that catalyze the phosphorylation of proteins, and in particular the hydroxy groups on tyrosine, serine, and threonine residues of proteins. The consequences of this seemingly simple activity are significant. Cell differentiation and proliferation (i.e., virtually all aspects of cell life, in one-way or another) depend on protein kinase activity. Furthermore, abnormal protein kinase activity has been related to a host of disorders, ranging from relatively non-life threatening diseases, such as psoriasis, to extremely virulent diseases, such as glioblastoma (brain cancer).

Protein kinases can be categorized as receptor type or non-receptor type. Receptor-type tyrosine kinases have an extracellular, a transmembrane, and an intracellular portion, while non-receptor type tyrosine kinases are wholly intracellular. They are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HER3, and HER4. Ligands of this subfamily of receptors identified so far include epithelial growth factor, TGF-alpha, amphiregulin, HB-EGF, betacellulin, and heregulin. Another subfamily of these receptor-type tyrosine kinases is the insulin subfamily, which includes INS-R, IGF-IR, and IR-R. The PDGF subfamily includes the PDGF-alpha and beta receptors, CSFIR, c-kit, and FLK-11. In addition, there is the FLK family, which is comprised of the kinase insert domain receptor (KDR), fetal liver kinase-1 (FLK-1), fetal liver kinase-4 (FLK-4), and the fms-like tyrosine kinase-1 (flt-1). The PDGF and FLK families are usually considered together due to the similarities of the two groups. (For a detailed discussion of the receptor-type tyrosine kinases, see Plowman et al., *DN&P* 7(6): 334-339, 1994, which is hereby incorporated by reference.)

The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. (For a more detailed discussion of the non-receptor type of tyrosine kinases, see Bolen, Oncogene, 8:2025-2031 (1993), which is hereby incorporated by reference.)

Since protein kinases and their ligands play critical roles in various cellular activities, deregulation of protein kinase enzymatic activity can lead to altered cellular properties, such as uncontrolled cell growth associated with cancer. In addition to oncological indications, altered kinase signaling is implicated in numerous other pathological diseases. These include, but are not limited to: immunological disorders, cardiovascular diseases, inflammatory diseases, and degenerative diseases. Therefore, both receptor and non-receptor protein kinases are attractive targets for small molecule drug discovery.

One particularly attractive goal for therapeutic use of kinase modulation relates to oncological indications. For example, modulation of protein kinase activity for the treatment of cancer has been demonstrated successfully with the FDA approval of Gleevec® (imatinib mesylate, produced by Novartis Pharmaceutical Corporation of East Hanover, N.J.) for the treatment of Chronic Myeloid Leukemia (CML) and gastrointestinal stroma cancers. Gleevec is a selective Abl kinase inhibitor.

Modulation (particularly inhibition) of cell proliferation and angiogenesis, two key cellular processes needed for tumor growth and survival (Matter A. *Drug Disc Technol* 2001 6, 1005-1024), is an attractive goal for the development of small-molecule drugs. Anti-angiogenic therapy represents a potentially important approach for the treatment of solid tumors and other diseases associated with dysregulated vascularization, including ischemic coronary artery disease, diabetic retinopathy, psoriasis and rheumatoid arthritis. Cell anti-proliferative agents are desirable to slow or stop the growth of tumors.

One particularly attractive target for small-molecule modulation, with respect to antiangiogenic and anti-proliferative activity is MEK. Inhibition of MEK1 (MAPK/ERK Kinase) is a promising strategy to control the growth of tumors that are dependent on aberrant ERK/MAPK pathway signaling (Solit et al., 2006; Wellbrock et al., 2004). The MEK-ERK signal transduction cascade is a conserved pathway, which regulates cell growth, proliferation, differentiation, and apoptosis in response to growth factors, cytokines, and hormones. This pathway operates downstream of Ras which is often upregulated or mutated in human tumors. It has been demonstrated that MEK is a critical effector of Ras function. The ERK/MAPK pathway is upregulated in 30% of all tumors and oncogenic activating mutations in K-Ras and B-Raf have been identified in 22% and 18% of all cancers respectively (Allen et al., 2003; Bamford S, 2004; Davies et al., 2002; Malumbres and Barbacid, 2003). It has been reported that a large portion of human cancers, including 66% (B-Raf) of malignant melanomas, 60% (K-Ras) and 4% (B-Raf) of pancreatic cancers, 50% of colorectal cancers (colon, in particular, K-Ras: 30%, B-Raf: 15%), 20% (K-Ras) of lung cancers, 27% (B-Raf) papillary and anaplastic thyroid cancer, and 10-20% (B-Raf) of endometriod ovarian cancers, harbor activating Ras and Raf mutations. It has been shown that inhibition of the ERK pathway, and in particular inhibition of MEK kinase activity, results in anti-metastatic and anti-angiogenic effects largely due to a reduction of cell-cell contact and motility as well as downregulation of vascular endothelial growth factor (VEGF) expression. Furthermore, expression of dominant negative MEK, or ERK reduced the transforming ability of mutant Ras as seen in cell culture and in primary and metastatic growth of human tumor xenografts in vivo. Therefore, the MEK-ERK signal transduction pathway is an appropriate pathway to target for therapeutic intervention.

The Bcl-2 family of proteins regulates programmed cell death triggered by developmental cues and in response to multiple Stress signals (Cory. S., and Adams, J. M., Nature Reviews Cancer 2 (2002) 647-656; Adams, Genes und Development 17 (2003) 2481-2495; Danial, N. N., and Korsmeyer, S. J., Cell 116 (2004) 205-219). Whereas cell survival is promoted by Bcl-2 itself and several close relatives (Bcl-xL, Bcl-W, Mcl-1, and Al), which bear three or four conserved Bcl-2 homology (BH) regions, apoptosis is driven by two other subfamilies. The initial signal for cell death is conveyed by the diverse group of BH3-only proteins, including Bad, Bid. Bim, Puma and Noxa, which have in common only the small BH3 interaction domain (Huang and Strasser, Cell 103 (2000) 839-842). However, Bax or Bak, multi-domain proteins containing BH1-BH3, are required for commitment to cell death (Cheng, et al., Molecular Cell 8 (2001) 705-711; Wei, M. C., et al., Science 292 (2001) 727-730; Zong, W. X., et al., Genes and Development 15 148 (2001) 1-1486). When activated, they can permeabilize the outer membrane of mitochondria and release pro-apoptogenic factors (e.g., cytochrome C) needed to activate the caspases that dismantle the cell (Wang, K., Genes and Development 15 (2001) 2922-2933; (Adams, 2003 supra); Green, D. R, and Kroemer, G., Science 305 (2004) 626-629).

Interactions between members of these three factions of the Bcl-2 family may dictate whether a cell lives or dies. When BH3-only proteins have been activated, for example, in response to DNA damage, they can bind via their BH3 domain to a groove on their pro-survival relatives (Sattler, et al., Science 275 (1997) 983-986). How the BH3-only and Bcl-2-like proteins control the activation of Bax and Bak, however, remains poorly understood (Adams, 2003 supra). Most attention has focused on Bax. This soluble monomeric protein (Hsu, Y. T., et al., Journal of Biological Chemistry 272 (1997) 13289-1 3834; Wolter, K. G., et al., Journal of Cell Biology 139 (1997) 1281-92) normally has its membrane targeting domain inserted into its groove, probably accounting for its cytosolic localization (Nechushtan. A., et al., EMBO Journal 18 (1999) 2330-2341: Suzuki, et al., Cell 103 (2000) 645-654: Schinzel, A., et al., J Cell Biol 164 (2004) 1021-1032). Several unrelated peptides/proteins have been proposed to modulate Bax activity (see, e.g., Lucken-Ardjomande, S., and Martinou, J. C., J Cell Sci 118 (2005) 473-483), but their physiological relevance remains to be established. Alternatively, Bax may be activated via direct engagement by certain BH3-only proteins (Lucken-Ardjomande, S., and Martinou, J. C. 2005 supra), the best documented being a truncated form of Bid, tBid (Wei. M. C., et al., Genes und Development 14 (2000) 2060-2071; Kuwana, T., et al., Cell 111 (2002) 331-342; Roucou, X., et al., Biochemical Journal 368 (2002) 915-921: Catron. P. F., et al., Mol Cell 16 (2004) 807-818). As discussed elsewhere (Adams 2003 supra), the oldest model, in which Bcl-2 directly engages Bax (Oltvai, Z. N., et al., Cell 74 (1993) 609-619), has become potentially problematic because Bcl-2 is membrane bound while Bax is cytosolic, and their interaction seems highly dependent on the detergents used for cell lysis (Hsu. Y. T., and Youle, 1997 supra). Nevertheless, it has been established that the BH3 region of Bax can mediate association with Bcl-2 (Zha, H, and Reed, J., Journal of Biological Chemistry 272 (1997) 31482-88: Wang, K., et al., Molecular and Cellular Biology 18 (1998) 6083-6089), and that Bcl-2 may prevent the oligomerization of Bax, even though no heterodimers can be detected (Mikhailov, V., et al., Journal of Biological Chemistry 276 (2001) 18361-18374). Thus, whether the pro-survival proteins restrain Bax activation directly or indirectly remains uncertain.

Although Bax and Bak seem in most circumstances to be functionally equivalent (Lindsten, T. et al., Molecular Cell 6 (2000) 1389-1399; Wei, M. C., et al., 2001 supra), substantial differences in their regulation would be expected from their distinct localization in healthy cells. Unlike Bax, which is largely cytosolic, Bak resides in complexes on the outer membrane of mitochondria and on the endoplasmic reticulum of healthy cells (Wei, M. C., et al., 2000 supra; Zong, W. X., et al., Journal of Cell Biology 162 (2003) 59-69). Nevertheless, on receipt of cytotoxic signals, both Bax and Bak change conformation, and Bax translocates to the organellar membranes, where both Bax and Bak then form homo-oligomers that can associate, leading to membrane permeabilization (Hsu. Y. T., et al., PNAS 94 (1997) 3668-3672; Wolter, K. G., et al., 1997 supra; Antonsson, B., et al., Journal of Biological Chemistry 276 (2001) 11615-11623; Nechushtan, A. et al., Journal of Cell Biology 153 (2001) 1265-1276: Wei, M. C., et al., 2001 supra; Mikhailov. V., et al., Journal of Biological Chemistry 278 (2003) 5367-5376).

There exist various Bcl-2 inhibitors, which all have the same property of inhibiting prosurvival members of the Bcl-2 family of proteins and are therefore promising candidates for the treatment of cancer. Such Bcl-2 inhibitors include, for example: Oblimersen, SPC-2996, RTA-402, Gossypol, AT-101, Obatoclax mesylate, A-371191, A-385358, A-438744, ABT-737, ABT-263, AT-101, BL-1, BL-193, GX-15-003, 2-Methoxyantimycin A3, HA-14-1, KF-67544, Purpurogallin, TP-TW-37, YC-137 and Z-24, and are described, for example, in Zhai, D., et al., Cell Death and Differentiation 13 (2006) 1419-1421.

SUMMARY OF THE INVENTION

The present invention is directed to a method of treating a proliferative disorder, the method comprising administering to a mammal in need thereof a therapeutically effective amount of a combination of a MEK inhibitor and a selective Bcl-2 inhibitor.

The present invention is further directed to a pharmaceutical product comprising (i) a first composition comprising [3,4-Difluoro-2-(2-fluoro-4-iodoanilino)phenyl]{3-hydroxy-3-[(2S)-piperidin-2-yl]azetidin-1-yl}methanone (cobimetinib) or a pharmaceutically acceptable salt thereof, and (ii) a second composition comprising 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy) benzamide (ABT-199) or a pharmaceutically acceptable salt thereof.

Other objects and features will be in part apparent and in part pointed out hereinafter.

BRIEF DESCRIPTION OF THE DRAWINGS

(FIG. 1A) The AML cell lines were treated with cobimetinib or venetoclax at 0.001, 0.01, 0.1 and 1.0 µM for 72 hrs. Calcusyn software was used to calculate the $IC_{50}$ values and combination index (CI) based on the luminescent intensity that correlated with number of viable cells determined by the CellTiter-Glo assay. P-ERK was determined using flow cytometry and relative median fluorescence intensity (R-MFI) was determined using MFI of p-ERK. Response patterns 1-5 were shown. (FIGS. 1B through 1L) Growth curves of representative cell lines from each response pattern.

(FIG. 2A) Primary AML peripheral blood mononuclear cells were cultured in serum-Free Expansion Medium (SFEM) supplemented with BIT 9500 Serum Substitute and cytokines including stem cell factor (100 ng/ml), Flt3 ligand (50 ng/ml), IL-3 (20 ng/ml) and G-CSF (20 ng/ml) as well as SRI (1 µM). After culture for 5 days, cells were stained with CD45-PE, Annexin-V-APC and DAPI–. The apoptotic leukemia blasts (CD45dimAnnexin-V+) were determined by flow cytometry. Results were expressed as percentage of specific apoptosis calculated by the formula: 100×(% apoptosis of treated cells–% apoptosis of control cells)/(100–% apoptosis of control cells), or % growth inhibition of control using the viable cell counts determined by Annexin-/DAPI. (FIG. 2B) Representative data from 3 AML samples were shown, for those displaying synergy. MNCs isolated from patients with AML (100,000) or healthy donors (50,000) were plated in methylcellulose medium (1 mL/well; Cat. 04435; STEMCELL Technologies Inc., Vancouver, BC, Canada) in triplicate per condition. Colonies were scored after 2 weeks of culture. (FIG. 2C). Clinical data and combination index values based on viable cell count.  p<0.01, * p<0.001.

(FIGS. 3A, 3B, 3C, and 3D) RPPA data demonstrate proteins differentially expressed in sensitive or resistant AML cell lines (to single drugs or combination) treated with cobimetinib or/and venetoclax at 0.5×, 1× and 2×$IC_{50}$ values for 24 hrs. Representative proteins that are differentially expressed between combination-sensitive and combination-resistant cells were shown. (FIG. 3E) The Bcl-2:BIM complex was measured by the MSD ELISA assay in AML cell lines, untreated, treated with venetoclax alone, treated with cobimetinib alone, or treated with cobimetinib/venetoclax at 1×$IC_{50}$ values for 4 hrs.

FIGS. 4A, 4B, and 4C demonstrate Mass cytometry analysis of intracellular proteins in cell sub-populations. Mononuclear cells from primary AML were treated with cobimetinib at 1.0 µM for 2 hrs followed by 10 minutes plus or minus stimulation with G-CSF (100 ng/ml). The SPADE tree was generated using markers including CD7, CD117, CD123, CD64, CD34, CD26, CD45, TIM3, CD33, CD19, CD56, CD2, CD15, CD41, CD38, CD166, CD3, CD90, CD11b, CD135 and HLA-DR. FIG. 4A depicts representative markers from among those markers tested. The greyscale color represents the expression levels of each indicated protein. (FIG. 4A) Bcl-2 family members at baseline in the gated stem/progenitor AML cell populations (AML4-295468: CD34+CD38+CD123+CD33+; AML 4366894: CD34+CD38-CD123+CD33+). (FIG. 4B) The median intensity of each protein in the gated cell populations mentioned above. (FIG. 4C) The intracellular signaling protein activation in the gated populations mentioned above.

(FIG. 5A) The luciferase intensity was quantified by serial bioluminescence imaging from 8 representative mice from 4 groups at week 5 post injection. (FIG. 5B) Overall survival rate in each group was estimated by the Kaplan-Meier method. $1\times10^6$ MOLM13-luci-GFP cells were injected into NSGS mice. Leukemia engraftment was confirmed on day 3 using Bioluminescence imaging (BLI). Mice were orally dosed daily with cobimetinib (10 mg/kg) or venetoclax (100 mg/kg) or in combination for 14 days. Luciferase intensity was shown on day 17 (FIG. 5C). Human CD45 engraftment in BM and spleen was determined by CyTOF. (FIG. 5D). The viable cell count was measured using Vi-Cell. (FIG. 5E). * *P: 0.01, ***P: 0.001.

DESCRIPTION OF THE EMBODIMENT(S) OF THE INVENTION

Figure 1A:
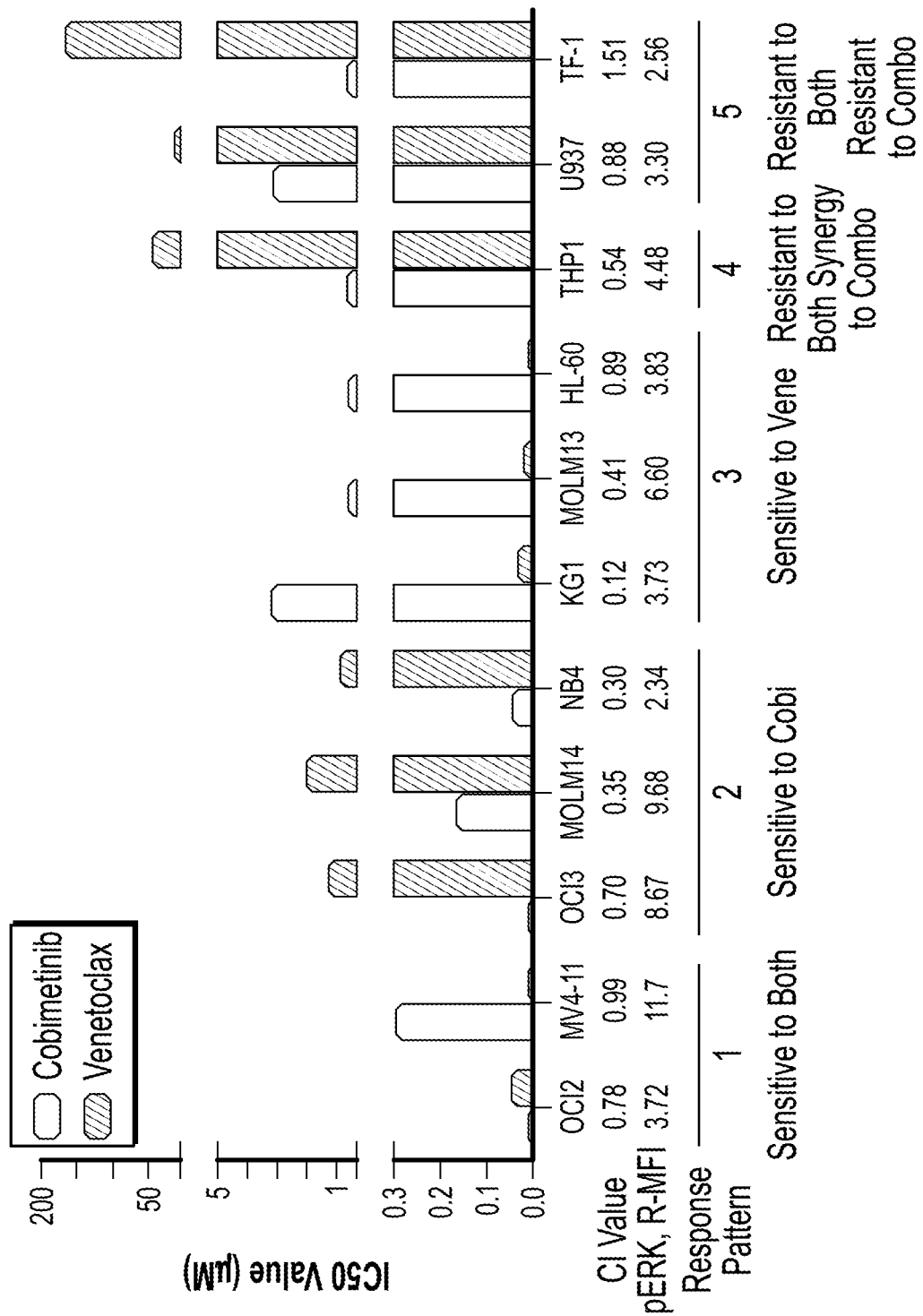
FIGS. 1A through 1L are graphs depicting in vitro cytotoxicity of cobimetinib and venetoclax against AML cell lines.
Figure 1B:
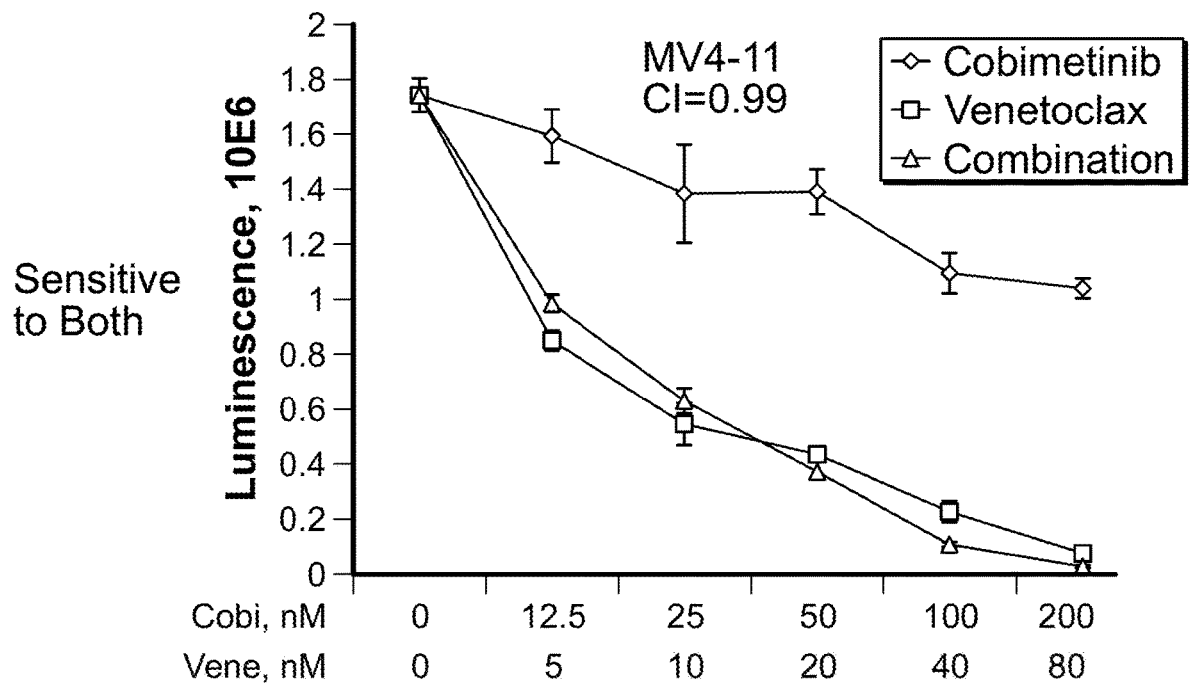
Figure 1C:
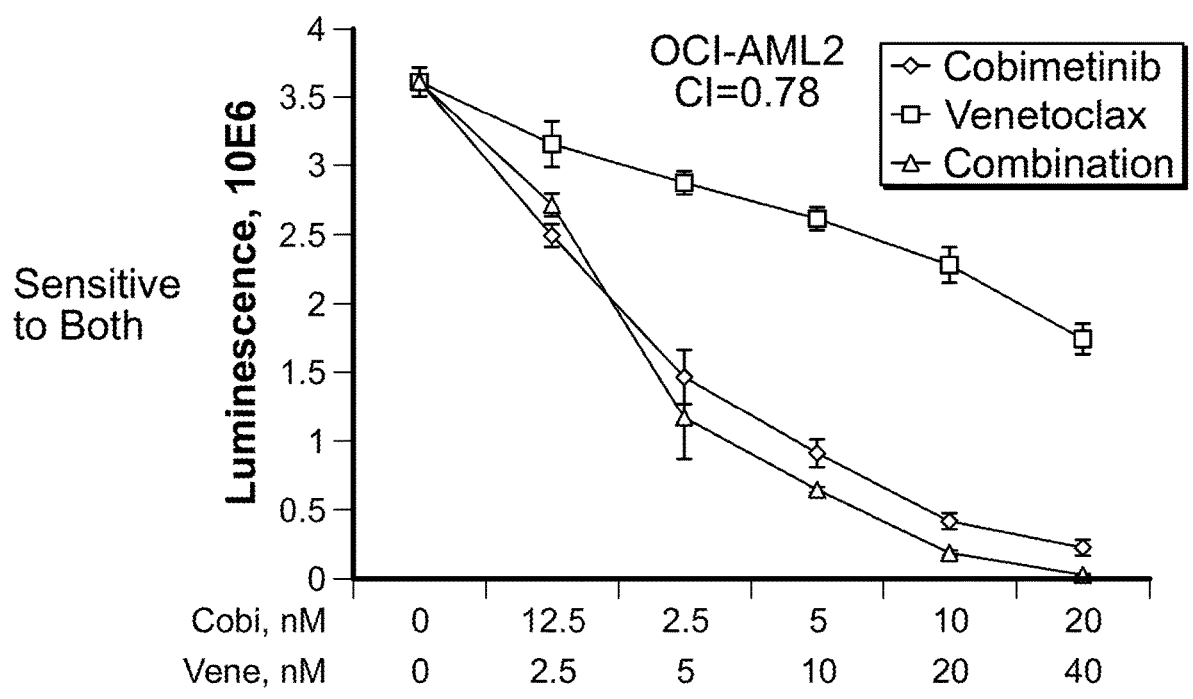
Figure 1D:
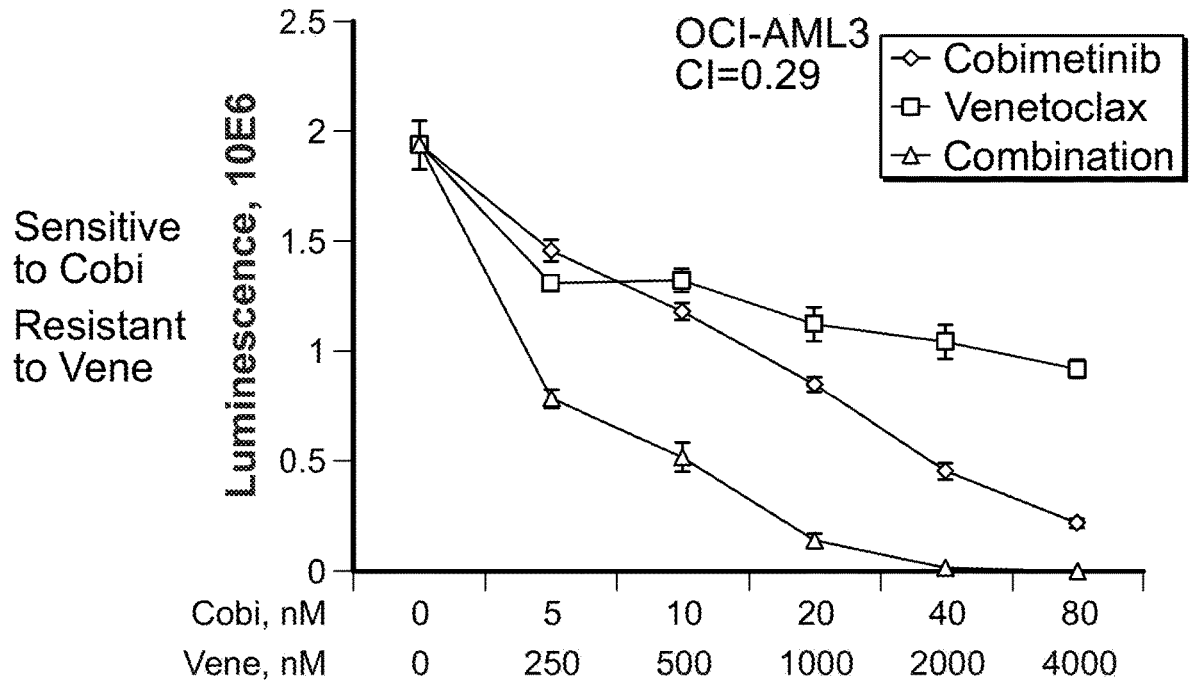
Figure 1E:
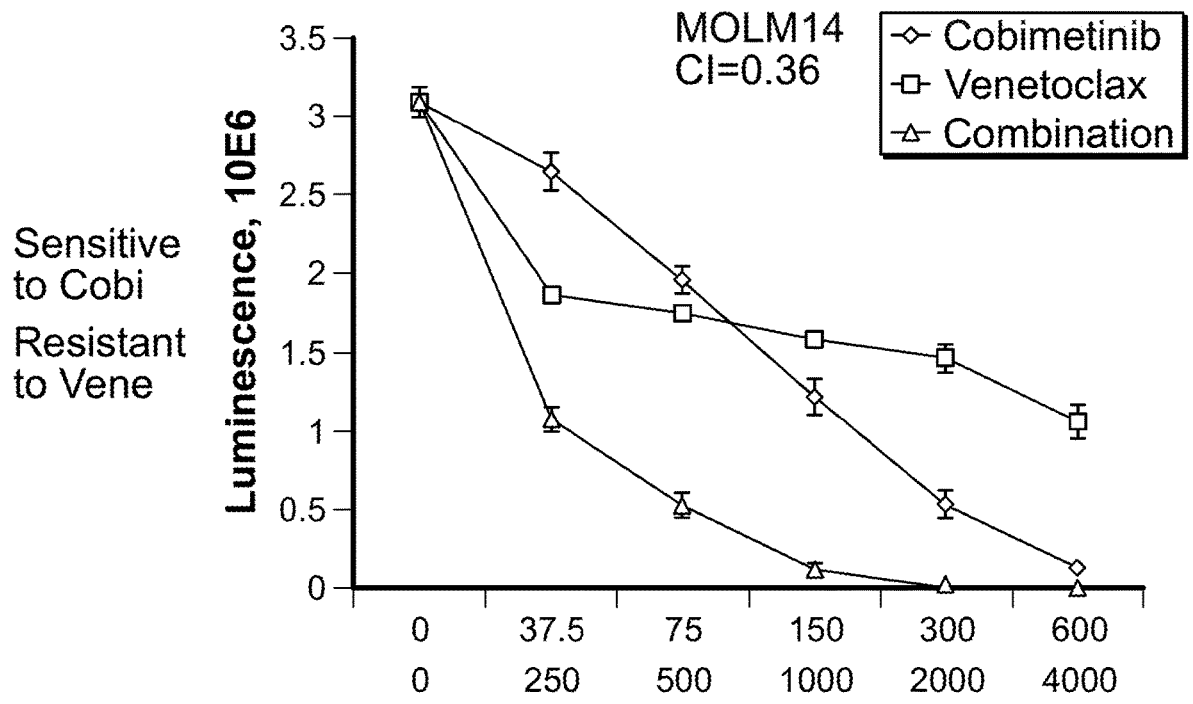
Figure 1F:
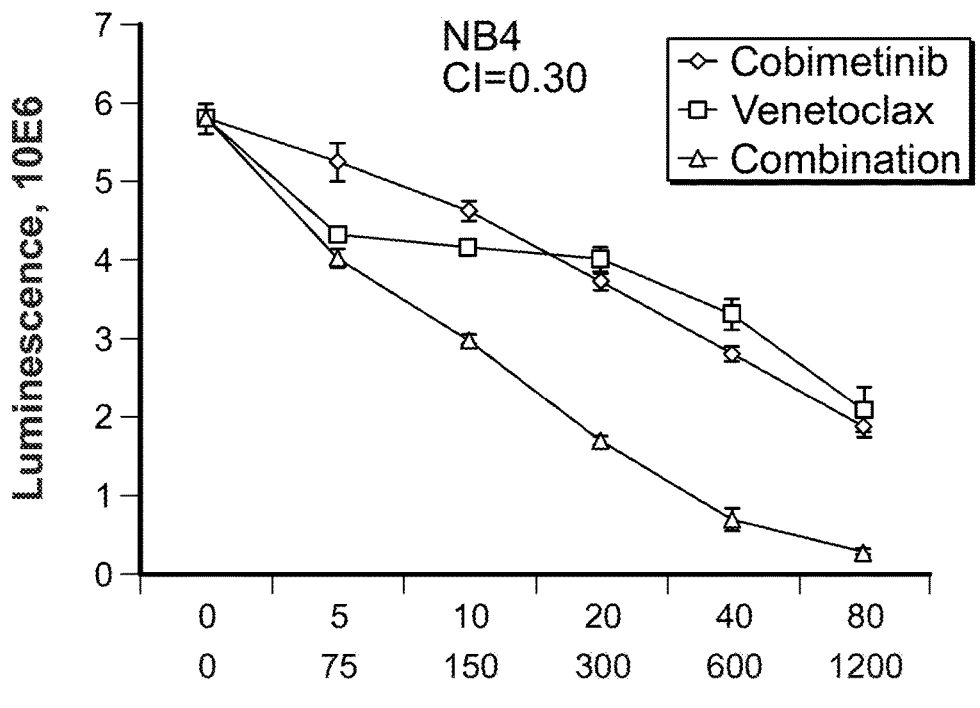
Figure 1G:
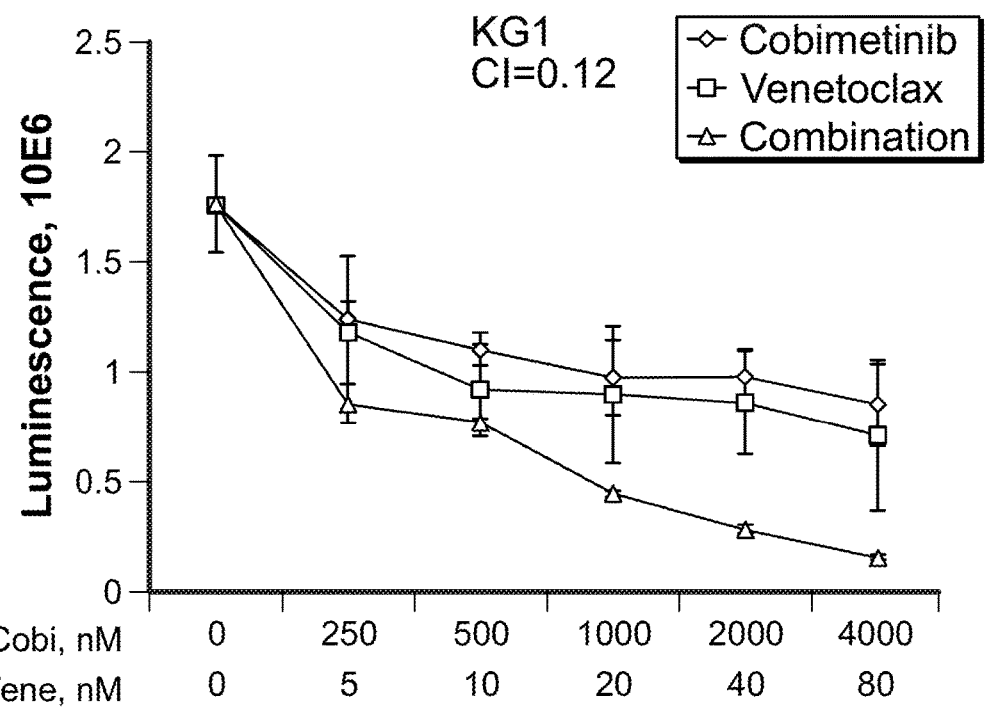
Figure 1H:
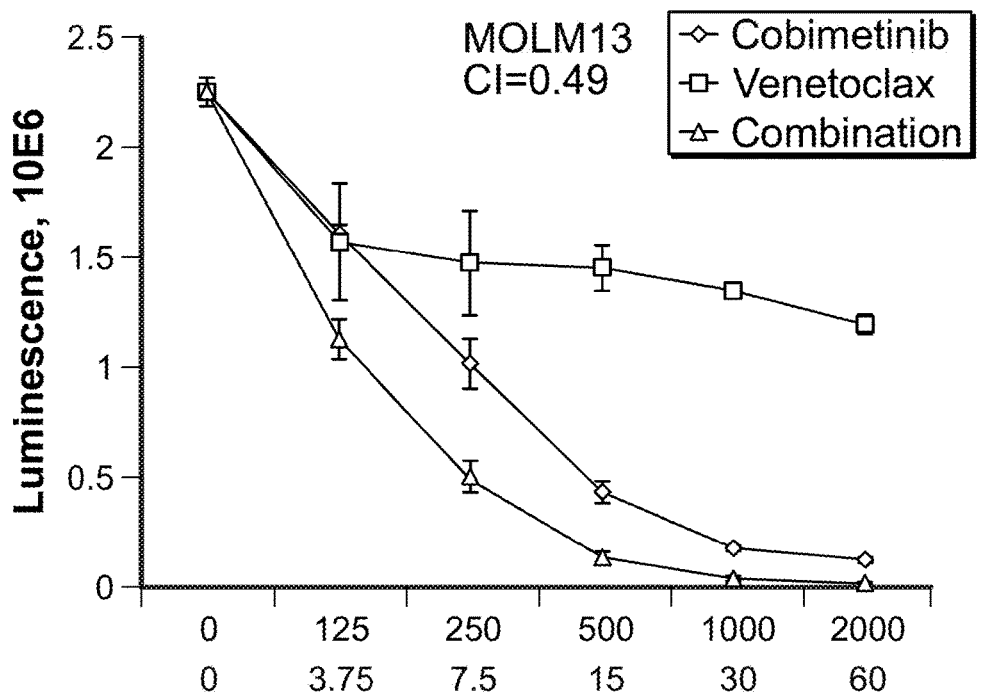
Figure 1I:
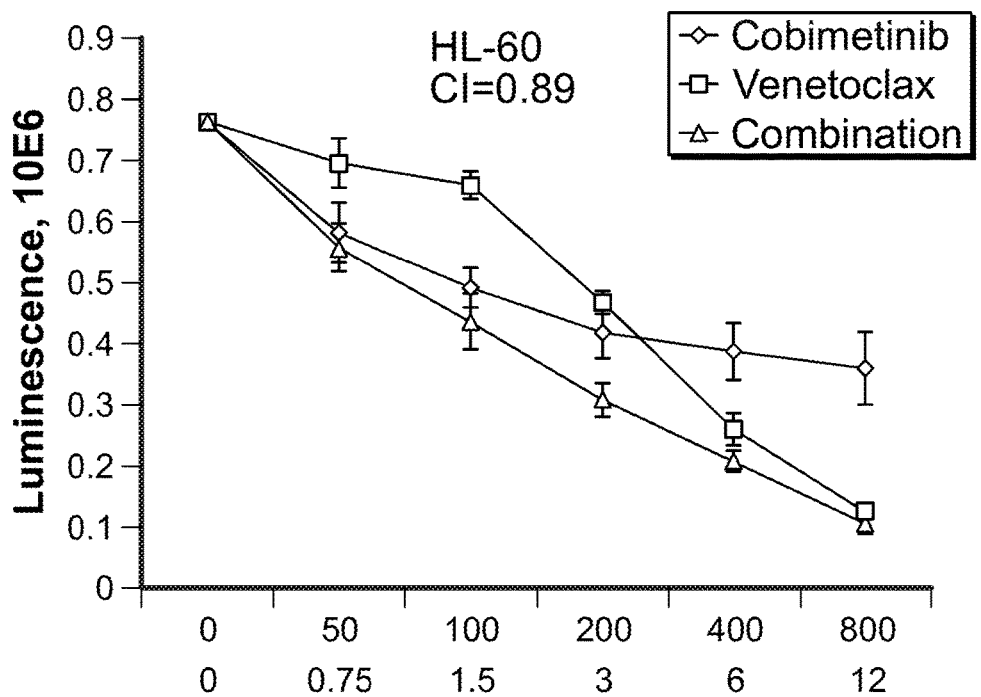
Figure 1J:
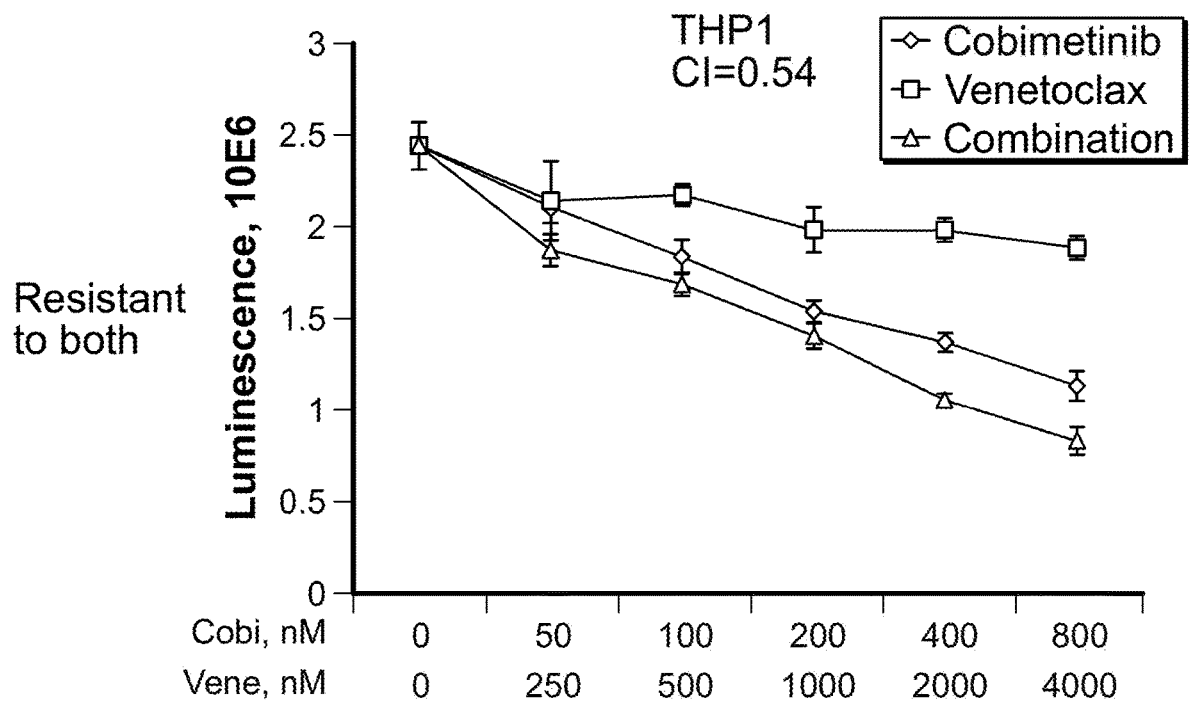
Figure 1K:
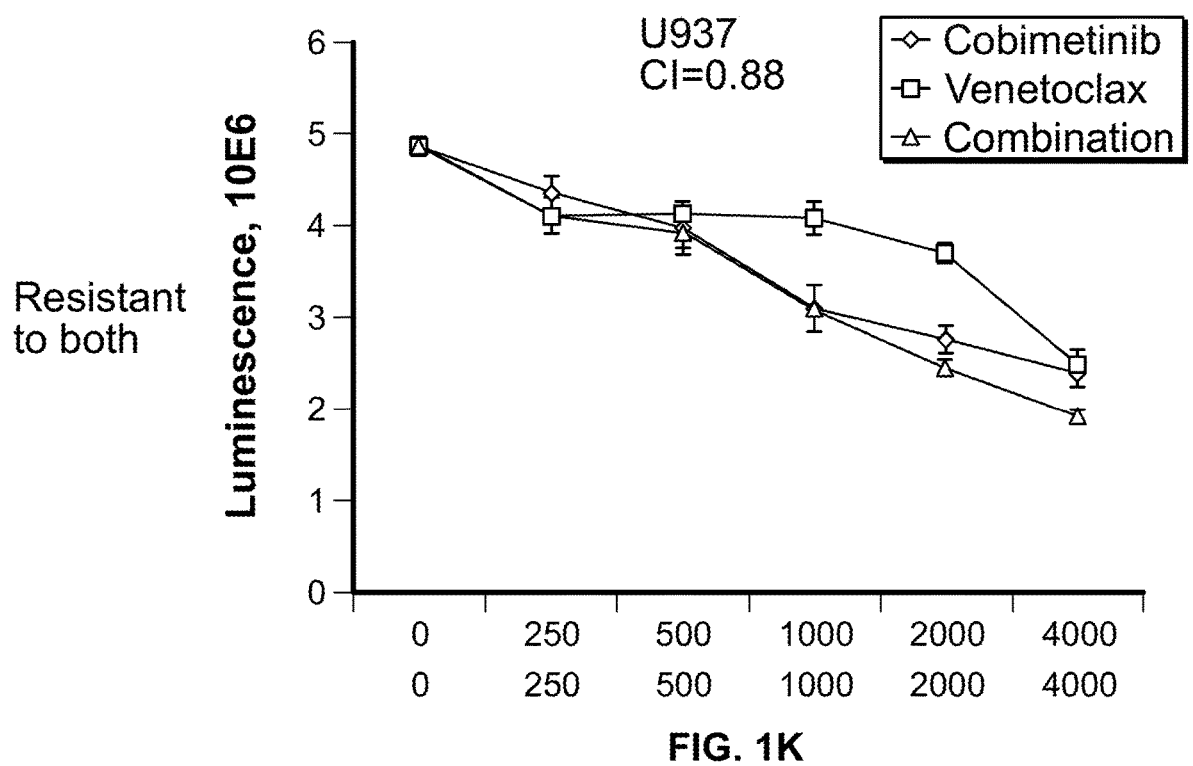
Figure 1L:
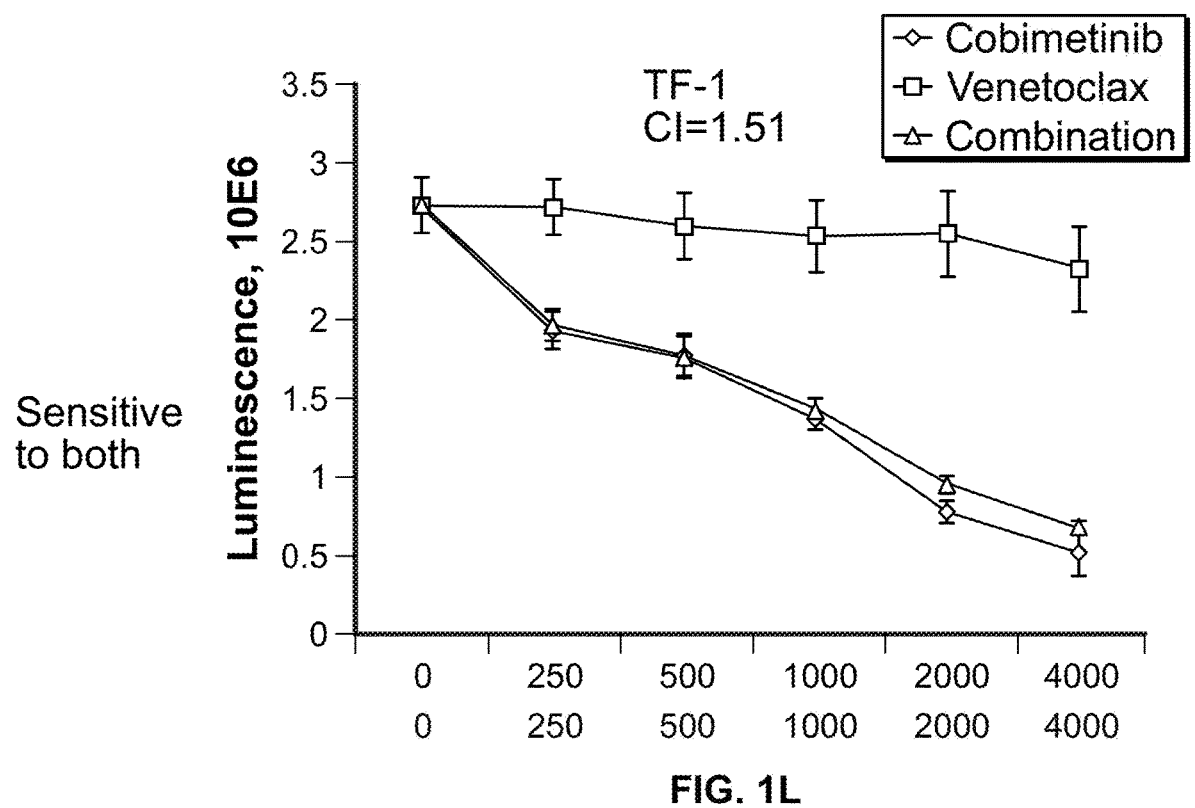

The present invention is directed to a combination therapy involving a selective Bcl-2 inhibitor and a MEK inhibitor for the treatment of a mammal, e.g., a human patient, in need of such a therapy. Pro-survival molecules including Bcl-2 play critical roles in leukemia transformation and chemoresistance. ABT-199 (also known as, and optionally referred to herein as, GDC-0199, or venetoclax) is an orally available BH3-mimetic that binds with high affinity to Bcl-2, but lacks affinity for Bcl-$X_L$ and Mcl-1. The anti-leukemia potency of venetoclax in acute myeloid leukemia (AML) models has recently been demonstrated (see, e.g., Pan et al., Cancer Discovery 2014). However, venetoclax poorly inhibits Mcl-1, causing resistance in leukemia cells that rely on Mcl-1 for survival. The RAF/MEK/ERK (MAPK) cascade is a major effector pathway in AML that is activated by upstream mutant proteins such as FLT3, KIT and RAS. Additionally, the MAPK pathway regulates Bcl-2 family proteins by stabilizing anti-apoptotic Mcl-1 and inactivating pro-apoptotic BIM. In some embodiments, the present invention is directed to a combination therapy that combines the anti-tumor effects of the concomitant Bcl-2 and MAPK blockade by venetoclax in combination with MEK1/2 inhibitor cobimetinib.

In some embodiment, the mammal, e.g., a human patient, in need of the combination therapy is suffering from cancer, such as acute myeloid leukemia. In some embodiments, the combination therapy involves administering a therapeutically effective amount of a selective Bcl-2 inhibitor and a therapeutically effective amount of a MEK inhibitor for the treatment of a mammal, e.g., a human patient, in need of such a therapy.

In some embodiments, the mammal, e.g., a human patient, in need of the combination therapy is suffering from cancer, such as multiple myeloma. In some embodiments, the combination therapy involves administering a therapeutically effective amount of a selective Bcl-2 inhibitor and a therapeutically effective amount of a MEK inhibitor for the treatment of a mammal, e.g., a human patient, in need of such a therapy.

In some embodiments, the selective Bcl-2 inhibitor comprises 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide (also known as, and optionally referred to herein as, venetoclax, or ABT-199, or GDC-0199) or a pharmaceutically acceptable salt thereof. In some embodiments, the combination therapy of the present invention involves administration of a therapeutically effective amount of 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide (venetoclax, or ABT-199/GDC-0199) or a pharmaceutically acceptable salt thereof to a mammal, e.g., a human patient, in need thereof. Venetoclax has the following structure:

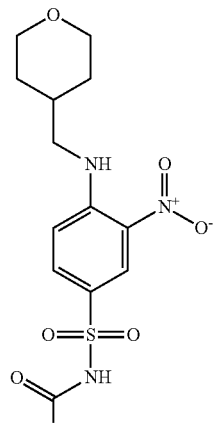

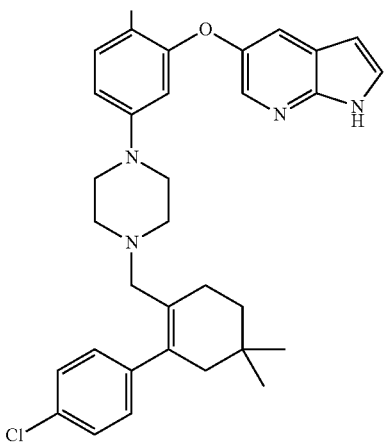

4-(4-{[2-(4-chlorophenyl)-4,4-dimethylcyclohex-1-en-1-yl]methyl}
piperazin-1-yl)-N-({3-nitro-4-[(tetrahydro-2H-pyran-4-ylmethyl)
amino]phenyl}sulfonyl)-2-(1H-pyrrolo[2,3-b]pyridin-5-yloxy)benzamide In some embodiments, the MEK inhibitor comprises [3,4-difluoro-2-(2-fluoro-4-iodoanilino)phenyl]{3-hydroxy-3-[(2S)-piperidin-2-yl]azetidin-1-yl} methanone (also known as, and optionally referred to herein as, cobimetinib, or GDC-0973) or a pharmaceutically acceptable salt thereof. In some embodiments, the combination therapy of the present invention involves administration of a therapeutically effective amount of [3,4-difluoro-2-(2-fluoro-4-iodoanilino)phenyl]{3-hydroxy-3-[(2S)-piperidin-2-yl]azetidin-1-yl}methanone (cobimetinib, or GDC-0973) or a pharmaceutically acceptable salt thereof to a mammal, e.g., a human patient, in need thereof. Cobimetinib has the following structure:

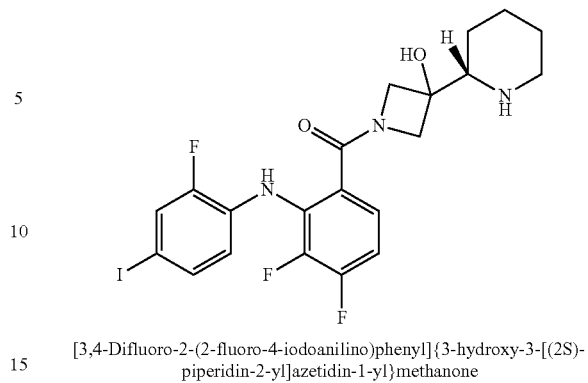

[3,4-Difluoro-2-(2-fluoro-4-iodoanilino)phenyl]{3-hydroxy-3-[(2S)-
piperidin-2-yl]azetidin-1-yl}methanone The name of this compound as generated using ACD/Labs naming software 8.00 release, product version 8.08 is 1-({3,4-difluoro-2-[(2-fluoro-4-iodophenyl)amino]phenyl}carbonyl)-3-[(2S)-piperidin-2-yl]azetidin-3-ol.

In some embodiments, the combination therapy comprises administering to a mammal, e.g., a human patient, in need of such a therapy a therapeutically effective amount of 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide (ABT-199) or a pharmaceutically acceptable salt thereof and a therapeutically effective amount of [3,4-Difluoro-2-(2-fluoro-4-iodoanilino)phenyl]{3-hydroxy-3-[(2S)-piperidin-2-yl]azetidin-1-yl}methanone (cobimetinib) or a pharmaceutically acceptable salt thereof. The patient in need of the combination therapy of the invention may be suffering from cancer. In some embodiments, the cancer is acute myeloid leukemia. In some embodiments, the cancer is multiple myeloma.

1. Definitions

The term "mammal" includes, but is not limited to, humans, mice, rats, guinea pigs, monkeys, dogs, cats, horses, cows, pigs, sheep, and poultry. The term patient refers to a mammal, and in one embodiment, the patient is a human male or a human female.

Herein, a "patient" (interchangeably termed "individual") is a human patient. The patient may be a "cancer patient", i.e. one who is suffering or at risk for suffering from one or more symptoms of cancer. A "subject" or an "individual" for purposes of treatment refers to any animal classified as a mammal, including humans, domestic and farm animals, and zoo, sports, or pet animals, such as dogs, horses, cats, cows, etc. Preferably, the mammal is human.

A "population" of patients refers to a group of patients with cancer, such as in a clinical trial, or as seen by oncologists following FDA approval for a particular indication, such as unresectable or metastatic melanoma cancer therapy.

A "disorder" is any condition that would benefit from treatment including, but not limited to, chronic and acute disorders or diseases including those pathological conditions which predispose the mammal to the disorder in question.

The terms "cell proliferative disorder" and "proliferative disorder" refer to disorders that are associated with some degree of abnormal cell proliferation. In one embodiment, the cell proliferative disorder is cancer. In one embodiment, the cell proliferative disorder is a tumor.

"Tumor," as used herein, refers to all neoplastic cell growth and proliferation, whether malignant or benign, and all pre-cancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. More particular examples of such cancers include, but not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma AIDS-related lymphoma and Waldenstrom's Macroglobulinemia); chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In certain embodiments, cancers that are amenable to treatment by the antibodies of the invention include breast cancer, colorectal cancer, rectal cancer, non-small cell lung cancer, glioblastoma, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, ovarian cancer, mesothelioma, and multiple myeloma. In some embodiments, the cancer is selected from: small cell lung cancer, glioblastoma, neuroblastomas, melanoma, breast carcinoma, gastric cancer, colorectal cancer (CRC), and hepatocellular carcinoma.

The term "treating" as used herein, unless otherwise indicated, means reversing, alleviating, inhibiting the progress of, or preventing, either partially or completely, the growth of tumors, tumor metastases, or other cancer-causing or neoplastic cells in a patient. The object is to prevent or slow down (lessen) an undesired physiological change or disorder, such as the growth, development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. For example, an individual is successfully "treated" if one or more symptoms associated with cancer are mitigated or eliminated, including, but are not limited to, reducing the proliferation of (or destroying) cancerous cells, decreasing symptoms resulting from the disease, increasing the quality of life of those suffering from the disease, decreasing the dose of other medications required to treat the disease, and/or prolonging survival of individuals. "Treatment" refers to both therapeutic treatment and prophylactic or preventative measures. "Treatment" can also mean prolonging survival as compared to expected survival if not receiving treatment. Those in need of treatment include those already having the condition or disorder, e.g., a patient with cancer.

The term "a method of treating" or its equivalent, when applied to, for example, cancer refers to a procedure or course of action that is designed to reduce or eliminate the number of cancer cells in a patient, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of a patient, is nevertheless deemed to induce an overall beneficial course of action. The terms "co-administration" or "co-administering" refer to the administration of said MEK inhibitor and said selective Bcl-2 inhibitor as two separate formulations or within one single formulation. The co-administration can be simultaneous or sequential in either order. In one further embodiment, there is a time period while both (or all) active agents simultaneously exert their biological activities. Said MEK inhibitor and said selective Bcl-2 inhibitor are co-administered either simultaneously or sequentially (e.g. via an intravenous (i.v.) through a continuous infusion (one for the MEK inhibitor and eventually one for the Bcl-2 inhibitor; or the Bcl-2 inhibitor is administered orally). When both therapeutic agents are co-administered sequentially the agents are administered in two separate administrations that are separated by a "specific period of time". The term specific period of time is meant anywhere from 1 hour to 15 days. For example, one of the agents can be administered within about 15, 14, 13, 12, 11, 10, 9, 8, 7, 6, 5, 4, 3, 2, or 1 day, or 24, 23, 22, 21, 20, 19, 18, 17, 16, 15, 14, 13, 12, 11, 10, 9, 8, 7, 6, 5, 4, 3, 2 or 1 hour from the administration of the other agent, and, in one embodiment, the specific period time is 10, 9, 8, 7, 6, 5, 4, 3, 2, or 1 day, or 24, 23, 22, 21, 20, 19, 18, 17, 16, 15, 14, 13, 12, 11, 10, 9, 8, 7, 6, 5, 4, 3, 2 or 1 hour.

To "inhibit" is to decrease or reduce an activity, function, and/or amount as compared to a reference.

For the purposes herein, a "previously treated" cancer patient has received prior cancer therapy. A "previously treated" unresectable or metastatic melanoma patient has received prior therapy for unresectable or metastatic melanoma.

A "cancer medicament" is a drug effective for treating cancer.

The terms "orally deliverable", "oral administration" and "orally administered" herein refer to administration to a subject per os (p.o.), that is, administration wherein the composition is immediately swallowed, for example with the aid of a suitable volume of water or other potable liquid. "Oral administration" is distinguished herein from intraoral administration, e.g., sublingual or buccal administration or topical administration to intraoral tissues such as periodontal tissues, that does not involve immediate swallowing of the composition.

The term "simultaneously" means at the same time or within a short period of time, usually less than 1 hour.

A dosing period as used herein is meant a period of time, during which each therapeutic agent has been administered at least once. A dosing cycle is usually about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, and, in one embodiment, 6, 7, 8, 9, 10, 11, 12, 13, or 14 days, for example, 7 or 14 days.

In certain embodiments, a dosing period is a dosing cycle.

It is self-evident that the pharmaceutically active agents are administered to the patient in a "therapeutically effective amount" (or simply "effective amount") which is the amount of the respective compound or combination that will elicit the biological or medical response of a tissue, system, animal or human that is being sought by the researcher, veterinarian, medical doctor or other clinician. The administration of an effective amount of a pharmaceutically active agent can be a single administration or split dose administration. A "split dose administration" is meant an effective amount is a split into multiple doses, preferably 2, and administered within 1 or 2 days. For example, if 100 mg of a selective Bcl-2 inhibitor is deemed effective, it can be administered in one 100 mg administration or two 50 mg administrations. Split dose administration is sometimes desirable at the beginning of a dosing period to reduce side effects. When an effective amount is administered in split dosing, it is still considered one administration of an effective amount. For example, when 100 mg is the effective amount of a selective Bcl-2 inhibitor and that amount is administered in two 50 mg doses over a period of time, e.g. 2 days, only one effective amount is administered during that period of time.

The term "pharmaceutical formulation" refers to a sterile preparation that is in such form as to permit the biological activity of the medicament to be effective, and which contains no additional components that are unacceptably toxic to a subject to which the formulation would be administered.

As used herein, a "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. A non-limiting list of exemplary pharmaceutically acceptable carriers is a buffer, excipient, stabilizer, or preservative. Except insofar as any conventional media or agent is incompatible with the active compound, use thereof in the compositions of the invention is contemplated. Supplementary active compounds can also be incorporated into the compositions.

The phrase "pharmaceutically acceptable salt" as used herein, refers to pharmaceutically acceptable organic or inorganic salts of a compound. Exemplary salts include, but are not limited to bismesylate, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

The desired pharmaceutically acceptable salt may be prepared by any suitable method available in the art. For example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. Acids which are generally considered suitable for the formation of pharmaceutically useful or acceptable salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1 19; P. Gould, International J. of Pharmaceutics (1986) 33 201 217; Anderson et al, The Practice of Medicinal Chemistry (1996), Academic Press, New York; Remington's Pharmaceutical Sciences, 18.sup.th ed., (1995) Mack Publishing Co., Easton Pa.; and in The Orange Book (Food & Drug Administration, Washington, D.C. on their website). These disclosures are incorporated herein by reference thereto.

II. Selective Bcl-2 Inhibitor

The combination therapy of the present invention involves the administration of a selective Bcl-2 inhibitor. Methods of treatment using selective Bcl-2 inhibitors are disclosed in U.S. Publication No. 2012/0129853, the disclosure of which is hereby incorporated by reference as if set forth in its entirety. In this regard, a selective Bcl-2 inhibitor is one which selectively binds to a particular protein within the Bcl-2 family. In some embodiments, the combination therapy of the present invention involves the administration of a selective Bcl-2 inhibitor that selectively inhibits Bcl-2 protein. For example, 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide (also known as, and optionally referred to as, venetoclax, or ABT-199/GDC-0199 is an orally available, potent and highly selective inhibitor of Bcl-2, a member of the Bcl-2 family of regulator proteins that regulate apoptosis. ABT-199 selectively binds to and elicits a response on Bcl-2 proteins at much lower concentrations than those required to bind to and elicit a response on Bcl-$x_L$. As such, when ABT-199 is administered to the patient, the inhibitor is more prone to inhibit Bcl-2, rather than Bcl-$x_L$. ABT-199 tends to have a competitive binding affinity ($K_i$) for Bcl-2 that is at least about 500, at least about 1000, at least about 2000, at least about 2500, at least about 3000, at least about 3500, and at least about 4000 times less than the binding affinity for Bcl-$X_L$. As such, even at low concentrations (i.e., picomolar concentrations), ABT-199 will bind to and inhibit the Bcl-2 protein.

In some embodiments, the selective Bcl-2 inhibitor comprises 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide (venetoclax, or ABT-199/GDC-0199) or a pharmaceutically acceptable salt thereof. In some embodiments, the combination therapy of the present invention involves administration of a therapeutically effective amount of 4-(4-{[2-(4-chlorophenyl)-4,4-dimethyl cyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide (venetoclax, or ABT-199/GDC-0199) or a pharmaceutically acceptable salt thereof to a mammal, e.g., a human patient, in need thereof. Venetoclax has the following structure:

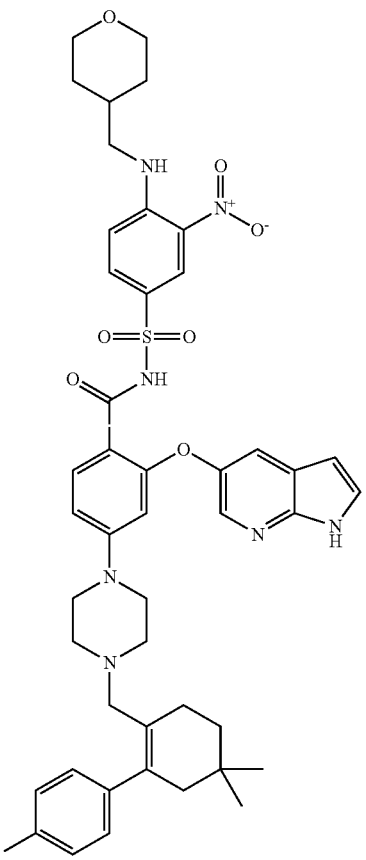

4-(4-{[2-(4-chlorophenyl)-4,4-dimethylcyclohex-1-en-1-yl]methyl}
piperazin-1-yl)-N-({3-nitro-4-[(tetrahydro-2H-pyran-4-ylmethyl)
amino]phenyl}sulfonyl)-2-(1H-pyrrolo[2,3-b]pyridin-5-yloxy)benzamide Venetoclax (or ABT-199/GDC-0199) may be formulated in its parent-compound form (i.e., as a free base), in a pharmaceutically acceptable salt form of the compound, or a combination of the parent-compound form and the pharmaceutically acceptable salt form. Additional suitable forms include the hydrate or solvated forms of ABT-199. In some embodiments, the ABT-199 may be a crystalline polymorph suitable for incorporation into a pharmaceutical composition further comprising a pharmaceutical acceptable excipient. Salts and crystalline forms of ABT-199 are disclosed in U.S. Publication No. 2012/0157470, the disclosure of which is hereby incorporated by reference as if set forth in its entirety. The phrase "pharmaceutically acceptable salt(s)", as used herein, means those salts of ABT-199 that are safe and effective for administration to a patient and that do not adversely affect the therapeutic qualities of the compound. Pharmaceutically acceptable salts include salts of acidic or basic groups present in compounds of the invention. Salts of ABT-199 can be prepared during isolation or following purification of the compounds.

Acid addition salts are those derived from reaction of Venetoclax (or ABT-199/GDC-0199) with an acid. For example, salts including the acetate, acid phosphate, adipate, alginate, ascorbate, bicarbonate, citrate, aspartate, benzoate, benzenesulfonate (besylate), bisulfate, bitartrate, butyrate, camphorate, camphorsulfonate, citrate, digluconate, ethanesulfonate, ethanedisulfonate, formate, fumarate, gentisinate, glycerophosphate, gluconate, glucaronate, glutamate, hemisulfate, heptanoate, hexanoate, hydrobromide, hydrochloride, hydroiodide, isonicotinate, 1-hydroxy-2-naphthoate, lactate, lactobionate, malate, maleate, malonate, mesitylenesulfonate, methanesulfonate, naphthalenesulfonate, nicotinate, nitrate, oxalate, p-toluenesulfonate, pamoate (i.e., 1,1'-methylene-bis-(2-hydroxy-3-naphthoate), pantothenate, pectinate, persulfate, phosphate, picrate, propionate, saccharate, salicylate, succinate, sulfate, tartrate, thiocyanate, trichloroacetate, trifluoroacetate, para-toluenesulfonate and undecanoate salts of a compound of ABT-199 can be used in a composition of the invention. Basic addition salts, including those derived from reaction of ABT-19) with the bicarbonate, carbonate, hydroxide or phosphate of cations such as aluminum, lithium, sodium, potassium, calcium, zinc, and magnesium, can likewise be used. (For a review on pharmaceutically acceptable salts see, e.g., Berge et al., 66 *J. Pharm. Sci.*, 1-19 (1977), incorporated herein by reference, in its entirety.)

Venetoclax (or ABT-199/GDC-0199) or a pharmaceutically acceptable salt thereof may present in a dosage form in an amount that can be therapeutically effective when the composition is administered to a subject in need thereof according to an appropriate regimen. Dosage amounts are expressed herein as parent-compound-equivalent amounts unless the context requires otherwise. Typically, a unit dose (the amount administered at a single time), which can be administered at an appropriate frequency, e.g., twice daily to once weekly, is about 10 to about 1,000 mg, depending on the compound in question. Where frequency of administration is once daily (q.d.), unit dose and daily dose are the same. Illustratively, the unit dose is typically about 25 to about 1,000 mg, more typically about 50 to about 500 mg, for example about 50, about 100, about 150, about 200, about 250, about 300, about 350, about 400, about 450 or about 500 mg. Where the dosage form comprises a capsule shell enclosing the dosage form, e.g., a solid dispersion, or a tablet wherein the dosage form (e.g., a solid dispersion) is formulated with other ingredients, a unit dose can be deliverable in a single dosage form or a plurality of dosage forms, most typically 1 to about 10 dosage forms.

The "therapeutically effective amount" of the venetoclax (or ABT-199/GDC-0199) or the pharmaceutically acceptable salt thereof refers to that amount of the compound being administered sufficient to prevent development of or alleviate to some extent one or more of the symptoms of the condition or disorder being treated. Therapeutically effective amounts of ABT-199 depend on the recipient of the treatment, the disorder being treated and the severity thereof, the composition containing the compound, the time of administration, the route of administration, the duration of treatment, the compound potency, its rate of clearance and whether or not another drug is co-administered. Generally, the methods of the current invention involve administering a dose of the selective Bcl-2 inhibitor ranging from about 0.001 mg/kg to about 1000 mg/kg. In one embodiment, the methods involve administering a dose of selective Bcl-2 inhibitor ranging from about 0.01 mg/kg to about 500 mg/kg. In a further embodiment, the methods involve administering a dose of ABT-199 ranging from about 0.1 mg/kg to about 300 mg/kg.

The methods of the current invention may have illustrated improved efficacy in treating disease states compared to methods currently known within the art due to the fact that ABT-199 may selectively inhibit the Bcl-2 protein. The Bcl-2 family of proteins is a group of proteins that have regulatory effects on many developmental and homeostasis functions, such as apoptosis (programmed cell death). The Bcl-2 family includes other proteins include $Bcl-x_L$ and Bcl-w. However, inhibition of the $Bcl-x_L$ protein has been shown to have an adverse impact on platelet counts, in some cases resulting in thrombocytopenia. The selective Bcl-2 inhibitor compounds have shown a higher binding affinity (as evidenced by lower $K_i$ values) for Bcl-2 compared to other Bcl-2 family proteins, such as $Bcl-x_L$ and Bcl-w. As such, the methods of the current invention provide the advantages of inhibition of the Bcl-2 protein, with a decreased risk of the adverse effects associated with $Bcl-x_L$ and Bcl-w inhibition, such as thrombocytopenia. This may allow for a more tolerable combination with other drugs such as cobimetinib. Additionally, ABT-199 is a more potent Bcl-2 inhibitor than some Bcl-2 inhibitors known in the art. Finally, it has been observed that acute myeloid leukemia cells are more dependent on Bcl-2 than $Bcl-X_L$ for survival, which is an unexpected finding in this field. The rationale of combination with cobimetinib is to treat tumors in which Bcl-2 and Mcl-1 are co-expressed.

The binding affinity for the various proteins is measured as a value of $K_i$, which represents the amount of the compound required to inhibit a physiologic process or compound (such as a protein) by 50%. See U.S. Publication No. 2012/0129853, the disclosure of which is hereby incorporated by reference as if set forth in its entirety. The selective Bcl-2 compounds used in the methods of the current invention generally have a binding affinity ($K_i$) of less than about 1 micromolar, less than about 500 nanomolar, less than about 400 nanomolar, less than about 300 nanomolar, less than about 200 nanomolar, less than about 100 nanomolar, less than about 50 nanomolar, less than about 25 nanomolar, less than about 10 nanomolar, less than about 5 nanomolar, less than about 1 nanomolar, less than about 900 picomolar, less than about 800 picomolar, less than about 700 picomolar, less than about 600 picomolar, less than about 500 picomolar, less than about 400 picomolar, less than about 300 picomolar, less than about 200 picomolar, and less than about 100 picomolar to Bcl-2.

III. Cobimetinib

Cobimetinib (also known as, and optionally referred to herein as, GDC-0973) is an orally available, potent, and highly selective inhibitor of MEK1 and MEK2. MEK1 and MEK2 are central components of the RAS/RAF pathway. Selective MEK inhibitors, including cobimetinib, are disclosed in U.S. Pat. No. 7,803,839, the disclosure of which is hereby incorporated by reference as if set forth in its entirety.

In some embodiments, the MEK inhibitor comprises [3,4-difluoro-2-(2-fluoro-4-iodoanilino)phenyl]{3-hydroxy-3-[(2S)-piperidin-2-yl]azetidin-1-yl}methanone (cobimetinib, or GDC-0973) or a pharmaceutically acceptable salt thereof. In some embodiments, the combination therapy of the present invention involves administration of a therapeutically effective amount of [3,4-difluoro-2-(2-fluoro-4-iodoanilino)phenyl]{3-hydroxy-3-[(2S)-piperidin-2-yl]azetidin-1-yl}methanone (cobimetinib, or GDC-0973) or a pharmaceutically acceptable salt thereof to a mammal, e.g., a human patient, in need thereof. Cobimetinib has the following structure:

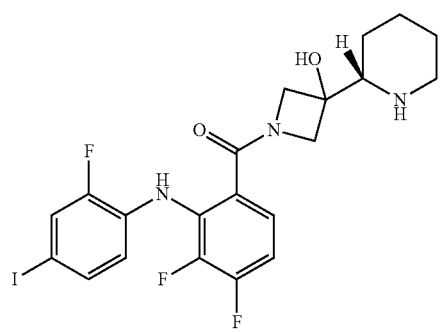

[3,4-Difluoro-2-(2-fluoro-4-iodoanilino)phenyl]{3-hydroxy-3-[(2S)-piperidin-2-yl]azetidin-1-yl}methanone Cobimetinib may be formulated in its parent-compound form (i.e., as a free base), in a pharmaceutically acceptable salt form of the compound, or a combination of the parent-compound form and the pharmaceutically acceptable salt form. Additional suitable forms include the hydrate or solvated forms of cobimetinib. In some embodiments, the cobimetinib may be a crystalline polymorph suitable for incorporation into a pharmaceutical composition further comprising a pharmaceutical acceptable excipient. Salts and crystalline forms of cobimetinib are disclosed in U.S. Pat. No. 7,803,839 and International Application No. PCT/EP2013/067050 (published as WO 2014/027056), the disclosures of which are hereby incorporated by reference as if set forth in their entirety. The phrase "pharmaceutically acceptable salt(s)", as used herein, means those salts of cobimetinib that are safe and effective for administration to a patient and that do not adversely affect the therapeutic qualities of the compound. Pharmaceutically acceptable salts include salts of acidic or basic groups present in compounds of the invention. Salts of cobimetinib can be prepared during isolation or following purification of the compounds.

Pharmaceutically acceptable salts are described herein and known in the art. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy- 3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion. If the compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. Acids which are generally considered suitable for the formation of pharmaceutically useful or acceptable salts from basic pharmaceutical compounds are discussed, for example, by: P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1 19; P. Gould. International J. of Pharmaceutics (1986) 33 201 217; Anderson et al, The Practice of Medicinal Chemistry (1996), Academic Press, New York: Remington's Pharmaceutical Sciences, 18th ed., (1995) Mack Publishing Co., Easton Pa.; and in The Orange Book (Food & Drug Administration, Washington, D.C. on their website). If the compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

Cobimetinib or a pharmaceutically acceptable salt thereof may present in a dosage from in an amount that can be therapeutically effective when the composition is administered to a subject in need thereof according to an appropriate regimen. Dosage amounts are expressed herein as parent-compound-equivalent amounts unless the context requires otherwise. Typically, a unit dose (the amount administered at a single time), which can be administered at an appropriate frequency, e.g., twice daily to once weekly, is about 10 to about 1,000 mg, depending on the compound in question. Where frequency of administration is once daily (q.d.), unit dose and daily dose are the same. Illustratively, the unit dose is typically about 25 to about 1,000 mg, more typically about 50 to about 500 mg, for example about 50, about 100, about 150, about 200, about 250, about 300, about 350, about 400, about 450 or about 500 mg. Where the dosage form comprises a capsule shell enclosing the dosage form, e.g., a solid dispersion, or a tablet wherein the dosage form, e.g., a solid dispersion is formulated with other ingredients, a unit dose can be deliverable in a single dosage form or a plurality of dosage forms, most typically 1 to about 10 dosage forms.

The "therapeutically effective amount" of cobimetinib or the pharmaceutically acceptable salt thereof refers to that amount of the compound being administered sufficient to prevent development of or alleviate to some extent one or more of the symptoms of the condition or disorder being treated. Therapeutically effective amounts of cobimetinib depend on the recipient of the treatment, the disorder being treated and the severity thereof, the composition containing the compound, the time of administration, the route of administration, the duration of treatment, the compound potency, its rate of clearance and whether or not another drug is co-administered. Generally, the methods of the current invention involve administering a dose of cobimetinib ranging from about 0.001 mg/kg to about 1000 mg/kg. In one embodiment, the methods involve administering a dose of cobimetinib ranging from about 0.01 mg/kg to about 500 mg/kg. In a further embodiment, the methods involve administering a dose of cobimetinib ranging from about 0.1 mg/kg to about 300 mg/kg.

IV. Pharmaceutical Formulations

Typically, the concentration of drug or combination of drugs in the pharmaceutical formulation is at least about 1%, e.g., about 1% to about 50%, by parent-compound-equivalent weight, but lower and higher concentrations can be acceptable or achievable in specific cases. Illustratively, the drug concentration in various embodiments is at least about 2%, e.g., about 2% to about 50%, or at least about 5%, e.g., about 5% to about 40%, for example about 5%, about 10%, about 15%, about 20%, about 25%, about 30%, about 35% or about 40%, by parent-compound-equivalent weight. In some embodiments, the drug concentration may be between about 5% and about 15%, such as between about 5% and about 12%, such as about 5%, about 6%, about 7%, about 8%, about 9%, about 10%, about 11%, or about 12%.

Orally deliverable solid dosage forms of the invention include but are not limited to capsules, dragees, granules, pills, powders and tablets. Excipients commonly used to formulate such dosage forms include encapsulating materials or formulation additives such as absorption accelerators, antioxidants, binders, buffers, coating agents, coloring agents, diluents, disintegrating agents, emulsifiers, extenders, fillers, flavoring agents, humectants, lubricants, preservatives, propellants, releasing agents, sterilizing agents, sweeteners, solubilizers and mixtures thereof. Many excipients have two or more functions in a pharmaceutical composition. Characterization herein of a particular excipient as having a certain function, e.g., diluent, disintegrant, binding agent, etc., should not be read as limiting to that function. Further information on excipients can be found in standard reference works such as *Handbook of Pharmaceutical Excipients*. 3rd ed. (Kibbe, ed. (2000), Washington: American Pharmaceutical Association).

In some embodiments, a suitable formulation may be prepared as a solid dispersion, e.g., by a melting-extrusion process or by a solvent evaporation process. The solid dispersion may be administered to a patient in need thereof, or the solid dispersion may be tabletted with further pharmaceutically acceptable excipients.

The melting-extrusion process (meltrex) is disclosed in U.S. Publication No. 2012/0108590, the disclosure of which is hereby incorporated by reference as if set forth in its entirety. The meltrex process comprises: (a) subjecting to elevated temperature (i) an active pharmaceutical ingredient (API) or a pharmaceutically acceptable salt thereof. (ii) a pharmaceutically acceptable water-soluble polymeric carrier and (iii) a pharmaceutically acceptable surfactant to provide an extrudable semi-solid mixture; (b) extruding the semi-solid mixture, for example through a die; and (c) cooling the resulting extrudate to provide a solid matrix comprising the polymeric carrier and the surfactant and having the compound or salt thereof dispersed in an essentially non-crystalline form therein. A "melt" herein is a liquid or semi-solid (e.g., rubbery) state induced by elevated temperature wherein it is possible for a first component to become homogeneously distributed in a matrix comprising a second component. Typically, the second (matrix) component, for example a polymeric carrier, is in such a state and other components, for example including a compound of Formula I or a salt thereof, dissolve in the melt, thus forming a solution. By "elevated temperature" herein is meant a temperature above a softening point of the polymeric carrier, as affected by other components if present, such as plasticizers or surfactants.

The solvent evaporation process is disclosed in U.S. Publication No. 2012/0277210, the disclosure of which is hereby incorporated by reference as if set forth in its entirety. The solvent evaporation process comprises: (a) dissolving (i) an active pharmaceutical ingredient (API) or a pharmaceutically acceptable salt thereof, (ii) a pharmaceutically acceptable water-soluble polymeric carrier and (iii) a pharmaceutically acceptable surfactant in a suitable solvent; and (b) removing the solvent to provide a solid matrix comprising the polymeric carrier and the surfactant and having the compound or salt thereof dispersed in an essentially non-crystalline form therein.

Suitable diluents illustratively include, either individually or in combination, lactose, including anhydrous lactose and lactose monohydrate; lactitol; maltitol; mannitol; sorbitol; xylitol; dextrose and dextrose monohydrate; fructose; sucrose and sucrose-based diluents such as compressible sugar, confectioner's sugar and sugar spheres; maltose; inositol; hydrolyzed cereal solids; starches (e.g., corn starch, wheat starch, rice starch, potato starch, tapioca starch, etc.), starch components such as amylose and dextrates, and modified or processed starches such as pregelatinized starch; dextrins; celluloses including powdered cellulose, microcrystalline cellulose, silicified microcrystalline cellulose, food grade sources of α- and amorphous cellulose and powdered cellulose, and cellulose acetate; calcium salts including calcium carbonate, tribasic calcium phosphate, dicalcium phosphate (e.g., dibasic calcium phosphate dihydrate), monobasic calcium sulfate monohydrate, calcium sulfate and granular calcium lactate trihydrate; magnesium carbonate; magnesium oxide; bentonite; kaolin; sodium chloride; and the like. Such diluents, if present, typically constitute in total about 1% to about 95%, for example about 5% to about 50%, or about 10% to about 30%, by weight of the composition. The diluent or diluents selected preferably exhibit suitable flow properties and, where tablets are desired, compressibility.

Microcrystalline cellulose and silicified microcrystalline cellulose are particularly useful diluents, and are optionally used in combination with a water-soluble diluent such as mannitol. Illustratively, a suitable weight ratio of microcrystalline cellulose or silicified microcrystalline cellulose to mannitol is about 10:1 to about 1:1, but ratios outside this range can be useful in particular circumstances.

Suitable disintegrants include, either individually or in combination, polymeric materials such as starches including pregelatinized starch and sodium starch glycolate; clays; magnesium aluminum silicate; cellulose-based disintegrants such as powdered cellulose, microcrystalline cellulose, methylcellulose, low-substituted hydroxypropylcellulose, carmellose, carmellose calcium, carmellose sodium and croscarmellose sodium; alginates; povidone; crospovidone; polacrilin potassium; gums such as agar, guar, locust bean, karaya, pectin and tragacanth gums; colloidal silicon dioxide; and the like. One or more disintegrants, if present, typically constitute in total about 0.2% to about 30%, for example about 0.5% to about 20%, or about 1% to about 10%, by weight of the composition.

Sodium starch glycolate is a particularly useful disintegrant, and typically constitutes in total about 1% to about 20%, for example about 2% to about 15%, or about 5% to about 10%, by weight of the composition.

Binding agents or adhesives are useful excipients, particularly where the composition is in the form of a tablet. Such binding agents and adhesives should impart sufficient cohesion to the blend being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; glucose; polydextrose; starch including pregelatinized starch; gelatin; modified celluloses including methylcellulose, carmellose sodium, hydroxypropylmethylcellulose (HPMC), hydroxypropylcellulose, hydroxyethylcellulose and ethylcellulose; dextrins including maltodextrin; zein; alginic acid and salts of alginic acid, for example sodium alginate; magnesium aluminum silicate; bentonite; polyethylene glycol (PEG); polyethylene oxide; guar gum; polysaccharide acids; polyvinylpyrrolidone (povidone or PVP), for example povidone K-15, K-30 and K-29/32; polyacrylic acids (carbomers); polymethacrylates; and the like. One or more binding agents and/or adhesives, if present, typically constitute in total about 0.5% to about 25%, for example about 1% to about 15%, or about 1.5% to about 10%, by weight of the composition.

Povidone and hydroxypropylcellulose, either individually or in combination, are particularly useful binding agents for tablet formulations, and, if present, typically constitute about 0.5% to about 15%, for example about 1% to about 10%, or about 2% to about 8%, by weight of the composition.

Wetting agents, e.g., solubilizers, can be added to the formulation if desired, in addition to the surfactant component of the solid dispersion. Non-limiting examples of surfactants that can be used as wetting agents include, either individually or in combination, quaternary ammonium compounds, for example benzalkonium chloride, benzethonium chloride and cetylpyridinium chloride; dioctyl sodium sulfosuccinate; polyoxyethylene alkylphenyl ethers, for example nonoxynol 9, nonoxynol 10 and octoxynol 9; poloxamers (polyoxyethylene and polyoxypropylene block copolymers); polyoxyethylene fatty acid glycerides and oils, for example polyoxyethylene (8) caprylic/capric mono- and diglycerides, polyoxyethylene (35) castor oil and polyoxyethylene (40) hydrogenated castor oil; polyoxyethylene alkyl ethers, for example ceteth-10, laureth-4, laureth-23, oleth-2, oleth-10, oleth-20, steareth-2, steareth-10, steareth-20, steareth-100 and polyoxyethylene (20) cetostearyl ether; polyoxyethylene fatty acid esters, for example polyoxyethylene (20) stearate, polyoxyethylene (40) stearate and polyoxyethylene (100) stearate; sorbitan esters, for example sorbitan monolaurate, sorbitan monooleate, sorbitan monopalmitate and sorbitan monostearate; polyoxyethylene sorbitan esters, for example polysorbate 20 and polysorbate 80; propylene glycol fatty acid esters, for example propylene glycol laurate; sodium lauryl sulfate; fatty acids and salts thereof, for example oleic acid, sodium oleate and triethanolamine oleate; glyceryl fatty acid esters, for example glyceryl monooleate, glyceryl monostearate and glyceryl palmitostearate; α-tocopherol polyethylene glycol (1000) succinate (TPGS); tyloxapol; and the like. One or more wetting agents, if present, typically constitute in total about 0.1% to about 15%, for example about 0.2% to about 10%, or about 0.5% to about 7%, by weight of the composition, excluding surfactant present in the solid dispersion.

Nonionic surfactants, more particularly poloxamers, are examples of wetting agents that can be useful herein. Illustratively, a poloxamer such as Pluronic™ F127, if present, can constitute about 0.1% to about 10%, for example about 0.2% to about 7%, or about 0.5% to about 5%, by weight of the composition, excluding surfactant present in the solid dispersion.

Lubricants reduce friction between a tableting mixture and tableting equipment during compression of tablet formulations. Suitable lubricants include, either individually or in combination, glyceryl behenate; stearic acid and salts thereof, including magnesium, calcium and sodium stearates; hydrogenated vegetable oils; glyceryl palmitostearate; talc; waxes; sodium benzoate; sodium acetate; sodium fumarate; sodium stearyl fumarate; PEGs (e.g., PEG 4000 and PEG 6000); poloxamers; polyvinyl alcohol; sodium oleate; sodium lauryl sulfate; magnesium lauryl sulfate; and the like. One or more lubricants, if present, typically constitute in total about 0.05% to about 10%, for example about 0.1% to about 5%, or about 0.2% to about 2%, by weight of the composition. Sodium stearyl fumarate is a particularly useful lubricant.

Anti-adherents reduce sticking of a tablet formulation to equipment surfaces. Suitable anti-adherents include, either individually or in combination, talc, colloidal silicon dioxide, starch, DL-leucine, sodium lauryl sulfate and metallic stearates. One or more anti-adherents, if present, typically constitute in total about 0.05% to about 10%, for example about 0.1% to about 7%, or about 0.2% to about 5%, by weight of the composition. Colloidal silicon dioxide is a particularly useful anti-adherent.

Glidants improve flow properties and reduce static in a tableting mixture. Suitable glidants include, either individually or in combination, colloidal silicon dioxide, starch, powdered cellulose, sodium lauryl sulfate, magnesium trisilicate and metallic stearates. One or more glidants, if present, typically constitute in total about 0.05% to about 10%, for example about 0.1% to about 7%, or about 0.2% to about 5%, by weight of the composition, excluding glidant present in the solid dispersion. Colloidal silicon dioxide is a particularly useful glidant.

Other excipients such as buffering agents, stabilizers, antioxidants, antimicrobials, colorants, flavors and sweeteners are known in the pharmaceutical art and can be used in compositions of the present invention. Tablets can be uncoated or can comprise a core that is coated, for example with a nonfunctional film or a release-modifying or enteric coating. Capsules can have hard or soft shells comprising, for example, gelatin (in the form of hard gelatin capsules or soft elastic gelatin capsules), starch, carrageenan and/or HPMC, optionally together with one or more plasticizers.

According to some embodiments of the present invention, a pharmaceutical product is provided, the pharmaceutical product comprising (i) a first composition comprising [3,4-Difluoro-2-(2-fluoro-4-iodoanilino)phenyl]{3-hydroxy-3-[(2S)-piperidin-2-yl]azetidin-1-yl}methanone (cobimetinib) or a pharmaceutically acceptable salt thereof, and (ii) a second composition comprising 4-(4-{[2-(4-chlorophenyl)-4,4-dimethylcyclohex-1-en-1-yl]methyl}piperazin-1-yl)-N-({(3-nitro-4-[(tetrahydro-2H-pyran-4-ylmethyl)amino]phenyl}sulfonyl)-2-(1H-pyrrolo[2,3-b]pyridin-5-yloxy)benzamide (ABT-199) or a pharmaceutically acceptable salt thereof. As set forth above, in some embodiments, the first composition further comprises a pharmaceutically acceptable excipient. In some embodiments, the second composition further comprises a pharmaceutically acceptable excipient. In some embodiments, the first composition and the second composition are the same. In some embodiments, the first composition and the second composition are different.

V. Indications

In some embodiments, the method of the present invention involves the administration to a mammal, e.g., a human patient, in need of such a therapy a therapeutically effective amount of 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide (venetoclax, or ABT-199/GDC-0199) or a pharmaceutically acceptable salt thereof and a therapeutically effective amount of [3,4-difluoro-2-(2-fluoro-4-iodoanilino)phenyl]{3-hydroxy-3-[(2S)-piperidin-2-yl]azetidin-1-yl}methanone (cobimetinib, or GDC-0973) or a pharmaceutically acceptable salt thereof to treat a disease during which is overexpressed one or more of antiapoptotic Bcl-2 protein, antiapoptotic Bcl-X, protein and antiapoptotic Bcl-w protein.

In another embodiment, a composition of the invention is administered in a therapeutically effective amount to a subject in need thereof to treat a disease of abnormal cell growth and/or dysregulated apoptosis.

Examples of such diseases include, but are not limited to, cancer, mesothelioma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, colon cancer, rectal cancer, cancer of the anal region, stomach cancer, gastrointestinal (gastric, colorectal and/or duodenal) cancer, chronic lymphocytic leukemia, acute lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular (hepatic and/or biliary duct) cancer, primary or secondary central nervous system tumor, primary or secondary brain tumor, Hodgkin's disease, chronic or acute leukemia, chronic myeloid leukemia, lymphocytic lymphoma, lymphoblastic leukemia, follicular lymphoma, lymphoid malignancies of T-cell or B-cell origin, melanoma, multiple myeloma, oral cancer, non-small-cell lung cancer, prostate cancer, small-cell lung cancer, cancer of the kidney and/or ureter, renal cell carcinoma, carcinoma of the renal pelvis, neoplasms of the central nervous system, primary central nervous system lymphoma, non-Hodgkin's lymphoma, spinal axis tumors, brain stem glioma, pituitary adenoma, adrenocortical cancer, gall bladder cancer, cancer of the spleen, cholangiocarcinoma, fibrosarcoma, neuroblastoma, retinoblastoma or a combination thereof.

In a more particular embodiment, the method of the present invention involves the administration to a mammal, e.g., a human patient, in need of such a therapy a therapeutically effective amount of 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide (venetoclax, or ABT-199/GDC-0199) or a pharmaceutically acceptable salt thereof and a therapeutically effective amount of [3,4-Difluoro-2-(2-fluoro-4-iodoanilino)phenyl]{3-hydroxy-3-[(2S)-piperidin-2-yl]azetidin-1-yl}methanone (cobimetinib, or GDC-0973) or a pharmaceutically acceptable salt thereof to treat to treat bladder cancer, brain cancer, breast cancer, bone marrow cancer, cervical cancer, chronic lymphocytic leukemia, acute lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small-cell lung cancer, prostate cancer, small-cell lung cancer or spleen cancer.

In a more particular embodiment, the method of the present invention involves the administration to a mammal, e.g., a human patient, in need of such a therapy a therapeutically effective amount of 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide (venetoclax, or ABT-199/GDC-0199) or a pharmaceutically acceptable salt thereof and a therapeutically effective amount of [3,4-Difluoro-2-(2-fluoro-4-iodoanilino)phenyl]{3-hydroxy-3-[(2S)-piperidin-2-yl]azetidin-1-yl}methanone (cobimetinib, or GDC-0973) or a pharmaceutically acceptable salt thereof to treat to treat acute myeloid leukemia.

In a more particular embodiment, the method of the present invention involves the administration to a mammal, e.g., a human patient, in need of such a therapy a therapeutically effective amount of 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1 H-pyrrolo[2,3-b]pyridin-5-yloxy) (venetoclax, or ABT-199/GDC-0199) or a pharmaceutically acceptable salt thereof and a therapeutically effective amount of [3,4-Difluoro-2-(2-fluoro-4-iodoanilino)phenyl]{3-hydroxy-3-[(2S)-piperidin-2-yl]azetidin-1-yl}methanone (cobimetinib, or GDC-0973) or a pharmaceutically acceptable salt thereof to treat to treat multiple myeloma.

For example, a method for treating mesothelioma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, colon cancer, rectal cancer, cancer of the anal region, stomach cancer, gastrointestinal (gastric, colorectal and/or duodenal) cancer, chronic lymphocytic leukemia, acute lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular (hepatic and/or biliary duct) cancer, primary or secondary central nervous system tumor, primary or secondary brain tumor, Hodgkin's disease, chronic or acute leukemia, chronic myeloid leukemia, lymphocytic lymphoma, lymphoblastic leukemia, follicular lymphoma, lymphoid malignancies of T-cell or B-cell origin, melanoma, multiple myeloma, oral cancer, non-small-cell lung cancer, prostate cancer, small-cell lung cancer, cancer of the kidney and/or ureter, renal cell carcinoma, carcinoma of the renal pelvis, neoplasms of the central nervous system, primary central nervous system lymphoma, non-Hodgkin's lymphoma, spinal axis tumors, brain stem glioma, pituitary adenoma, adrenocortical cancer, gall bladder cancer, cancer of the spleen, cholangiocarcinoma, fibrosarcoma, neuroblastoma, retinoblastoma or a combination thereof in a subject comprises administering to the subject therapeutically effective amounts of 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1 H-pyrrolo[2,3-b]pyridin-5-yloxy)benzamide (venetoclax, or ABT-199/GDC-0199) or a pharmaceutically acceptable salt thereof and a therapeutically effective amount of [3,4-Difluoro-2-(2-fluoro-4-iodoanilino)phenyl]{3-hydroxy-3-[(2S)-piperidin-2-yl]azetidin-1-yl}methanone (cobimetinib, or GDC-0973) or a pharmaceutically acceptable salt thereof.

In another embodiment, the method of the present invention involves the administration to a mammal, e.g., a human patient, in need of such a therapy a therapeutically effective amount of 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide (venetoclax, or ABT-199/GDC-0199) or a pharmaceutically acceptable salt thereof and a therapeutically effective amount of [3,4-Difluoro-2-(2-fluoro-4-iodoanilino)phenyl {3-hydroxy-3-1 (2S)-piperidin-2-yl]azetidin-1-yl}methanone (cobimetinib, or GDC-0973) or a pharmaceutically acceptable salt thereof to treat an immune or autoimmune disorder. Such disorders include acquired immunodeficiency disease syndrome (AIDS), autoimmune lymphoproliferative syndrome, hemolytic anemia, inflammatory diseases, thrombocytopenia, acute and chronic immune diseases associated with organ transplantation, Addison's disease, allergic diseases, alopecia, alopecia areata, atheromatous disease/arteriosclerosis, atherosclerosis, arthritis (including osteoarthritis, juvenile chronic arthritis, septic arthritis, Lyme arthritis, psoriatic arthritis and reactive arthritis), autoimmune bullous disease, abetalipoprotemia, acquired immunodeficiency-related diseases, acute immune disease associated with organ transplantation, acquired acrocyanosis, acute and chronic parasitic or infectious processes, acute pancreatitis, acute renal failure, acute rheumatic fever, acute transverse myelitis, adenocarcinomas, aerial ectopic beats, adult (acute) respiratory distress syndrome, AIDS dementia complex, alcoholic cirrhosis, alcohol-induced liver injury, alcohol-induced hepatitis, allergic conjunctivitis, allergic contact dermatitis, allergic rhinitis, allergy and asthma, allograft rejection, alpha-1-antitrypsin deficiency, Alzheimer's disease, amyotrophic lateral sclerosis, anemia, angina pectoris, ankylosing spondylitis-associated lung disease, anterior horn cell degeneration, antibody mediated cytotoxicity, antiphospholipid syndrome, anti-receptor hypersensitivity reactions, aortic and peripheral aneurysms, aortic dissection, arterial hypertension, arteriosclerosis, arteriovenous fistula, arthropathy, asthenia, asthma, ataxia, atopic allergy, atrial fibrillation (sustained or paroxysmal), atrial flutter, atrioventricular block, atrophic autoimmune hypothyroidism, autoimmune haemolytic anaemia, autoimmune hepatitis, type-1 autoimmune hepatitis (classical autoimmune or lupoid hepatitis), autoimmune mediated hypoglycemia, autoimmune neutropenia, autoimmune thrombocytopenia, autoimmune thyroid disease, B-cell lymphoma, bone graft rejection, bone marrow transplant (BMT) rejection, bronchiolitis obliterans, bundle branch block, burns, cachexia, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy-associated disorders, chlamydia, choleosatatis, chronic alcoholism, chronic active hepatitis, chronic fatigue syndrome, chronic immune disease associated with organ transplantation, chronic eosinophilic pneumonia, chronic inflammatory pathologies, chronic mucocutaneous candidiasis, chronic obstructive pulmonary disease (COPD), chronic salicylate intoxication, colorectal common varied immunodeficiency (common variable hypogammaglobulinemia), conjunctivitis, connective tissue disease-associated interstitial lung disease, contact dermatitis, Coombspositive hemolytic anemia, cor pulmonale, Creutzfeldt-Jakob disease, cryptogenic autoimmune hepatitis, cryptogenic fibrosing alveolitis, culture-negative sepsis, cystic fibrosis, cytokine therapy-associated disorders, Crohn's disease, dementia pugilistica, demyelinating diseases, dengue hemorrhagic fever, dermatitis, dermatitis scleroderma, dermatologic conditions, dermatomyositisi polymyositis-associated lung disease, diabetes, diabetic arteriosclerotic disease, diabetes mellitus, diffuse Lewy body disease, dilated cardiomyopathy, dilated congestive cardiomyopathy, discoid lupus erythematosus, disorders of the basal ganglia, disseminated intravascular coagulation, Down's Syndrome in middle age, drug-induced interstitial lung disease, drug-induced hepatitis, drug-induced movement disorders induced by drugs which block CNS dopamine receptors, drug sensitivity, eczema, encephalomyelitis, endocarditis, endocrinopathy, enteropathic synovitis, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, female infertility, fibrosis, fibrotic lung disease, fungal sepsis, gas gangrene, gastric ulcer, giant cell arteritis, glomerular nephritis, glomerulonephritides, Goodpasture's syndrome, goitrous autoimmune hypothyroidism (Hashimoto's disease), gouty arthritis, graft rejection of any organ or tissue, graft versus host disease, gram-negative sepsis, gram-positive sepsis, granulomas due to intracellular organisms, group B streptococci (GBS) infection, Graves' disease, hemosiderosis-associated lung disease, hairy cell leukemia, Hallerrorden-Spatz disease, Hashimoto's thyroiditis, hay fever, heart transplant rejection, hemachromatosis, hematopoietic malignancies (leukemia and lymphoma), hemolytic anemia, hemolytic uremic syndrome/thrombolytic thrombocytopenic purpura, hemorrhage, Henoch-Schoenlein purpura, hepatitis A, hepatitis B, hepatitis C, HIV infection/HIV neuropathy, Hodgkin's disease, hypoparathyroidism, Huntington's chorea, hyperkinetic movement disorders, hypersensitivity reactions, hypersensitivity pneumonitis, hyperthyroidism, hypokinetic movement disorders, hypothalamic-pituitary-adrenal axis evaluation, idiopathic Addison's disease, idiopathic leucopenia, idiopathic pulmonary fibrosis, idiopathic thrombocytopenia, idiosyncratic liver disease, infantile spinal muscular atrophy, infectious diseases, inflammation of the aorta, inflammatory bowel disease, insulin dependent diabetes mellitus, interstitial pneumonitis, iridocyclitis/uveitis/optic neuritis, ischemia-reperfusion injury, ischemic stroke, juvenile pernicious anemia, juvenile rheumatoid arthritis, juvenile spinal muscular atrophy, Kaposi's sarcoma, Kawasaki's disease, kidney transplant rejection, legionella, leishmaniasis, leprosy, lesions of the corticospinal system, linear IgA disease, lipidema, liver transplant rejection, Lyme disease, lymphederma, lymphocytic infiltrative lung disease, malaria, male infertility idiopathic or NOS, malignant histiocytosis, malignant melanoma, meningitis, meningococcemia, microscopic vasculitis of the kidneys, migraine headache, mitochondrial multisystem disorder, mixed connective tissue disease, mixed connective tissue disease-associated lung disease, monoclonal gammopathy, multiple myeloma, multiple systems degenerations (Mencel, Dejerine-Thomas, Shy-Drager and Machado-Joseph), myalgic encephalitis/Royal Free Disease, myasthenia gravis, microscopic vasculitis of the kidneys, *Mycobacterium avium* intracellulare, *Mycobacterium tuberculosis*, myelodyplastic syndrome, myocardial infarction, myocardial ischemic disorders, nasopharyngeal carcinoma, neonatal chronic lung disease, nephritis, nephrosis, nephrotic syndrome, neurodegenerative diseases, neurogenic I muscular atrophies, neutropenic fever, non-alcoholic steatohepatitis, occlusion of the abdominal aorta and its branches, occlusive arterial disorders, organ transplant rejection, orchitis/epidydimitis, orchitis/vasectomy reversal procedures, organomegaly, osteoarthrosis, osteoporosis, ovarian failure, pancreas transplant rejection, parasitic diseases, parathyroid transplant rejection, Parkinson's disease, pelvic inflammatory disease, pemphigus vulgaris, pemphigus foliaceus, pemphigoid, perennial rhinitis, pericardial disease, peripheral atherlosclerotic disease, peripheral vascular disorders, peritonitis, pernicious anemia, phacogenic uveitis, *Pneumocystis carinii* pneumonia, pneumonia, POEMS syndrome (polyneuropathy, organomegaly, endocrinopathy, monoclonal gammopathy, and skin changes syndrome), post-perfusion syndrome, post-pump syndrome, post-MI cardiotomy syndrome, postinfectious interstitial lung disease, premature ovarian failure, primary biliary cirrhosis, primary sclerosing hepatitis, primary myxoedema, primary pulmonary hypertension, primary sclerosing cholangitis, primary vasculitis, progressive supranuclear palsy, psoriasis, psoriasis type 1, psoriasis type 2, psoriatic arthropathy, pulmonary hypertension secondary to connective tissue disease, pulmonary manifestation of polyarteritis nodosa, post-inflammatory interstitial lung disease, radiation fibrosis, radiation therapy, Raynaud's phenomenon and disease, Raynoud's disease, Refsum's disease, regular narrow QRS tachycardia, Reiter's disease, renal disease NOS, renovascular hypertension, reperfusion injury, restrictive cardiomyopathy, rheumatoid arthritis-associated interstitial lung disease, rheumatoid spondylitis, sarcoidosis, Schmidt's syndrome, scleroderma, senile chorea, senile dementia of Lewy body type, sepsis syndrome, septic shock, seronegative arthropathies, shock, sickle cell anemia, Sjögren's disease-associated lung disease, Sjögren's syndrome, skin allograft rejection, skin changes syndrome, small bowel transplant rejection, sperm autoimmunity, multiple sclerosis (all subtypes), spinal ataxia, spinocerebellar degenerations, spondyloarthropathy, sporadic polyglandular deficiency type I, sporadic polyglandular deficiency type II, Still's disease, streptococcal myositis, stroke, structural lesions of the cerebellum, subacute sclerosing panencephalitis, sympathetic ophthalmia, syncope, syphilis of the cardiovascular system, systemic anaphylaxis, systemic inflammatory response syndrome, systemic onset juvenile rheumatoid arthritis, systemic lupus erythematosus, systemic lupus erythematosus-associated lung disease, lupus nephritis, systemic sclerosis, systemic sclerosis-associated interstitial lung disease, T-cell or FAB ALL, Takayasu's disease/arteritis, telangiectasia, Th2-type and Th1-type mediated diseases, thromboangitis obliterans, thrombocytopenia, thyroiditis, toxicity, toxic shock syndrome, transplants, trauma hemorrhage, type-2 autoimmune hepatitis (anti-LKM antibody hepatitis), type B insulin resistance with acanthosis nigricans, type III hypersensitivity reactions, type IV hypersensitivity, ulcerative colitic arthropathy, ulcerative colitis, unstable angina, uremia, urosepsis, urticaria, uveitis, valvular heart diseases, varicose veins, vasculitis, vasculitic diffuse lung disease, venous diseases, venous thrombosis, ventricular fibrillation, vitiligo acute liver disease, viral and fungal infections, vital encephalitis/aseptic meningitis, vital-associated hemaphagocytic syndrome, Wegener's granulomatosis, Wemicke-Korsakoff syndrome. Wilson's disease, xenograft rejection of any organ or tissue, yersinia and salmonella-associated arthropathy and the like.

VI. Combination Dosing Regimens

The terms "orally deliverable", "oral administration" and "orally administered" herein refer to administration to a subject per os (p.o.), that is, administration wherein the composition is immediately swallowed, for example with the aid of a suitable volume of water or other potable liquid. "Oral administration" is distinguished herein from intraoral administration, e.g., sublingual or buccal administration or topical administration to intraoral tissues such as periodontal tissues, that does not involve immediate swallowing of the composition.

The active ingredient form (e.g., parent compound or salt), the polymeric carrier(s), surfactant(s) and other optional ingredients should be selected, and relative amounts of these components should be used, to provide a solid dispersion or dosage form having acceptable bioabsorption when administered orally. Such bioabsorption can be evidenced, for example, by the pharmacokinetic (PK) profile of the solid dispersion or dosage form, more particularly by the $C_{max}$ or AUC, for example $AUC_{0-24}$ or $AUC_{0-\infty}$ at a particular dose or over a range of doses. Illustratively, bioavailability can be expressed as a percentage, for example using the parameter F, which computes AUC for oral delivery of a test composition as a percentage of AUC for intravenous (i.v.) delivery of the drug in a suitable solvent, taking into account any difference between oral and i.v. doses.

Bioavailability can be determined by PK studies in humans or in any suitable model species. For present purposes, a dog model is generally suitable. In various illustrative embodiments, compositions of the invention exhibit oral bioavailability of at least about 15%, at least about 20%, at least about 25% or at least about 30%, up to or exceeding about 50%, in a dog model, when administered as a single dose of about 2.5 to about 10 mg/kg to fasting or non-fasting animals.

Compositions embraced herein are useful for orally delivering a drug or a pharmaceutically acceptable salt thereof to a subject. Accordingly, a method of the invention for delivering such a drug to a subject comprises orally administering a composition as described above.

The subject can be human or non-human (e.g., a farm, zoo, work or companion animal, or a laboratory animal used as a model) but in an important embodiment the subject is a human patient in need of the drug, for example to treat a disease characterized by apoptotic dysfunction and/or over-expression of an anti-apoptotic Bcl-2 family protein. A human subject can be male or female and of any age. The patient is typically an adult, but a method of the invention can be useful to treat a childhood cancer such as leukemia, for example acute lymphocytic leukemia, in a pediatric patient.

The composition is normally administered in an amount providing a therapeutically effective daily dose of the drug. The term "daily dose" herein means the amount of drug administered per day, regardless of the frequency of administration. For example, if the subject receives a unit dose of 150 mg twice daily, the daily dose is 300 mg. Use of the term "daily dose" will be understood not to imply that the specified dosage amount is necessarily administered once daily. However, in a particular embodiment the dosing frequency is once daily (q.d.), and the daily dose and unit dose are in this embodiment the same thing.

What constitutes a therapeutically effective dose depends on the particular compound, the subject (including species and body weight of the subject), the disease (e.g., the particular type of cancer) to be treated, the stage and/or severity of the disease, the individual subject's tolerance of the compound, whether the compound is administered in monotherapy or in combination with one or more other drugs, e.g., other chemotherapeutics for treatment of cancer, and other factors. Thus the daily dose can vary within wide margins, for example from about 10 to about 1,000 mg. Greater or lesser daily doses can be appropriate in specific situations. It will be understood that recitation herein of a "therapeutically effective" dose herein does not necessarily require that the drug be therapeutically effective if only a single such dose is administered, typically therapeutic efficacy depends on the composition being administered repeatedly according to a regimen involving appropriate frequency and duration of administration. It is strongly preferred that, while the daily dose selected is sufficient to provide benefit in terms of treating the cancer, it should not be sufficient to provoke an adverse side-effect to an unacceptable or intolerable degree. A suitable therapeutically effective dose can be selected by the physician of ordinary skill without undue experimentation based on the disclosure herein and on art cited herein, taking into account factors such as those mentioned above. The physician may, for example, start a cancer patient on a course of therapy with a relatively low daily dose and titrate the dose upwards over a period of days or weeks, to reduce risk of adverse side-effects.

Illustratively, suitable doses are generally about 25 to about 1,000 mg/day, more typically about 50 to about 500 mg/day or about 200 to about 400 mg/day, for example about 50, about 100, about 150, about 200, about 250, about 300), about 350, about 400, about 450 or about 500 mg/day, administered at an average dosage interval of about 3 hours to about 7 days, for example about 8 hours to about 3 days, or about 12 hours to about 2 days. In most cases a once-daily (q.d.) administration regimen is suitable.

An "average dosage interval" herein is defined as a span of time, for example one day or one week, divided by the number of unit doses administered over that span of time. For example, where a drug is administered three times a day, around 8 am, around noon and around 6 pm, the average dosage interval is 8 hours (a 24-hour time span divided by 3). If the drug is formulated as a discrete dosage form such as a tablet or capsule, a plurality (e.g., 2 to about 10) of dosage forms administered at one time is considered a unit dose for the purpose of defining the average dosage interval.

Where the composition is in the form of a capsule, one to a small plurality of capsules can be swallowed whole, typically with the aid of water or other imbibable liquid to help the swallowing process. Suitable capsule shell materials include, without limitation, gelatin (in the form of hard gelatin capsules or soft elastic gelatin capsules), starch, carrageenan and HPMC.

Administration can be with or without food, i.e., in a non-fasting or fasting condition. It is generally preferred to administer the present compositions to a non-fasting patient.

VII. Additional Combinations

The combination therapy of the present invention may be suitable for use in with other chemotherapeutics or with ionizing radiation. Combination therapies illustratively include administration of a combination therapy of the present invention concomitantly with one or more of bortezomib, carboplatin, cisplatin, cyclophosphamide, dacarbazine, dexamethasone, docetaxel, doxorubicin, etoposide, fludarabine, irinotecan, paclitaxel, rapamycin, rituximab, vincristine and the like, for example with a polytherapy such as CHOP (cyclophosphamide+doxorubicin+vincristine+prednisone), RCVP (rituximab+cyclophosphamide+vincristine+prednisone), R-CHOP (rituximab+CHOP) or DA-EP-OCH-R (dose-adjusted etoposide, prednisone, vincristine, cyclophosphamide, doxorubicin and rituximab).

Additional examples of one or more therapeutic agents include, but are not limited to, alkylating agents, angiogenesis inhibitors, antibodies, antimetabolites, antimitotics, antiproliferatives, antivirals, aurora kinase inhibitors, other apoptosis inducing agents (for example, Bcl-xL, Bcl-w and Bfl-1 inhibitors), activators of a death receptor pathway, Bcr-Abl kinase inhibitors, BiTE (bi-specific T-cell engager) antibodies, antibody-drug conjugates, biological response modifiers, cyclin-dependent kinase (CDK) inhibitors, cell cycle inhibitors, cyclooxygenase-2 (COX-2) inhibitors, dual variable domain binding proteins (DVDs), human epidermal growth factor receptor 2 (ErbB2 or HER2neu) receptor inhibitors, growth factor inhibitors, heat shock protein (HSP)-90 inhibitors, histone deacetylase (HDAC) inhibitors, hormonal therapies, immunologicals, inhibitors of apoptosis proteins (IAPs), intercalating antibiotics, kinase inhibitors, kinesin inhibitors, JAK2 inhibitors, mammalian target of rapamycin (mTOR) inhibitors, microRNAs, mitogen-activated extracellular signal-regulated kinase (MEK) inhibitors, multivalent binding proteins, non-steroidal anti-inflammatory drugs (NSAIDs), poly-ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteasome inhibitors, purine analogs, pyrimidine analogs, receptor tyrosine kinase inhibitors, retinoids, deltoids, plant alkaloids, small inhibitory ribonucleic acids (siRNAs), topoisomerase inhibitors, ubiquitin ligase inhibitors, and the like.

BiTE antibodies are bi-specific antibodies that direct T-cells to attack cancer cells by simultaneously binding the two cells. The T-cell then attacks the target cancer cell. Examples of BiTE antibodies include, but are not limited to, adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (Sutton et al. (1997) *J. Immunol.* 158:5783-5790).

siRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200) bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mcl-1 have been shown to enhance the activity of ABT-263 or ABT-737 in various tumor cell lines (Tse et al. (2008) *Cancer Res.* 68:3421-3428 and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy-chain DVD polypeptides and two light-chain DVD polypeptides are referred to as DVD Ig's. Each half of a DVD Ig comprises a heavy-chain DVD polypeptide, a light-chain DVD polypeptide, and two antigen binding sites. Each binding site comprises a heavy-chain variable domain and a light-chain variable domain with a total of 6 CDRs involved in antigen binding per antigen binding site.

Alkylating agents include altretamine, AMD-473, AP-5280, apaziquone, bendamustine, brostallicin, busulfan, carboquone, carmustine (BCNU), chlorambucil, Cloretazine™ (laromustine, VNP 40101M), cyclophosphamide, dacarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, treosulfan, trofosfamide and the like.

Angiogenesis inhibitors include epidermal growth factor receptor (EGFR) inhibitors, endothelial-specific receptor tyrosine kinase (Tie-2) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include Alimta™ (pemetrexed disodium, LY231514, MTA), 5-azacitidine, Xeloda™ (capecitabine), carmofur, Leustat™ (cladribine), clofarabine, cytarabine, cytarabine ocfosfate, cytosine arabinoside, decitabine, deferoxamine, doxifluridine, eflomithine, EICAR (5-ethynyl-1-β-D-ribofuranosylimidazole-4-carboxamide), enocitabine, ethenylcytidine, fludarabine, 5-fluorouracil (5-FU) alone or in combination with leucovorin, Gemzar™ (gemcitabine), hydroxyurea, Alkeran™ (melphalan), mercaptopurine, 6-mercaptopurine riboside, methotrexate, mycophenolic acid, nelarabine, nolatrexed, ocfosfate, pelitrexol, pentostatin, raltitrexed, ribavirin, S-1, triapine, trimetrexate, TS-1, tiazofurin, tegafur, vidarabine, UFT and the like.

Antivirals include ritonavir, hydroxychloroquine and the like.

Aurora kinase inhibitors include ABT-348, AZD-1152, MLN-8054, VX-680, aurora A-specific kinase inhibitors, aurora B-specific kinase inhibitors, pan-aurora kinase inhibitors and the like.

Bcl-2 family protein inhibitors other than compounds of Formula I herein include AT-101 ((−)gossypol), Genasense™ Bcl-2-targeting antisense oligonucleotide (G3139 or oblimersen), IPI-194, IPI-565, ABT-737, ABT-263, GX-070 (obatoclax) and the like.

Bcr-Abl kinase inhibitors include dasatinib (BMS-354825), Gleevec™ (imatinib) and the like.

CDK inhibitors include AZD-5438, BMI-1040, BMS-387032, CVT-2584, flavopyridol, GPC-286199, MCS-5A, PD0332991, PHA-690509, seliciclib (CYC-202 or R-roscovitine), ZK-304709 and the like.

COX-2 inhibitors include ABT-963, Arcoxia™ (etoricoxib), Bextra™ (valdecoxib), BMS-347070, Celebrex™ (celecoxib), COX-189 (lumiracoxib), CT-3, Deramaxx™ (deracoxib), JTE-522, 4-methyl-2-(3,4-dimethylphenyl)-1-(4-sulfamoylphenyl)-1H-pyrrole, MK-663 (etoricoxib), NS-398, parecoxib, RS-57067, SC-58125, SD-8381, SVT-2016, S-2474, T-614, Vioxx™ (rofecoxib) and the like.

EGFR inhibitors include ABX-EGF, anti-EGFR immunoliposomes, EGF-vaccine, EMD-7200, Erbitux™ (cetuximab), HR3, IgA antibodies, Iressa™ (gefitinib), Tarceva™ (erlotinib or OSI-774), TP-38, EGFR fusion protein, Tykerb™ (lapatinib) and the like.

ErbB2 receptor inhibitors include CP-724714, CI-1033 (canertinib), Herceptin™ (trastuzumab), Tykerb™ (lapatinib), Omnitarg™ (2C4, petuzumab), TAK-165, GW-572016 (ionafamib), GW-282974, EKB-569, P1-166, dHER2 (HER2 vaccine), APC-8024 (HER2 vaccine), anti-HER/2neu bispecific antibody, B7.her2IgG3, AS HER2 trifunctional bispecific antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17AAG, CNF-101, CNF-1010, CNF-2024, 17-DMAG, geldanamycin, IPI-504, KOS-953, Mycograb™ (human recombinant antibody to HSP-90), nab-17AAG, NCS-683664, PU24FCl, PU-3, radicicol, SNX-2112, STA-9090, VER-49009 and the like.

Inhibitors of apoptosis proteins include HGS-1029, GDC-0145, GDC-0152, LCL-161, LBW-242 and the like.

Antibody-drug conjugates include anti-CD22-MC-MMAF, anti-CD22-MC-MMAE, anti-CD22-MCC-DM 1, CR-011-vcMMAE, PSMA-ADC, MEDI-547, SGN-19A, SGN-35, SGN-75 and the like.

Activators of death receptor pathway include TRAIL and antibodies or other agents that target TRAIL or death receptors (e.g., DR4 and DR5) such as apomab, conatumumab, ETR2-ST01, GDC0145 (lexatumumab), HGS-1029, LBY-135, PRO-1762, trastuzumab and the like.

Kinesin inhibitors include Eg5 inhibitors such as AZD-4877 and ARRY-520, CENPE inhibitors such as GSK-923295A, and the like.

JAK2 inhibitors include CEP-701 (lesaurtinib), XL019, INCB-018424 and the like. MEK inhibitors include ARRY-142886, ARRY-438162, PD-325901, PD-98059 and the like.

mTOR inhibitors include AP-23573, CCI-779, everolimus, RAD-001, rapamycin, temsirolimus, ATP-competitive TORC1/TORC2 inhibitors, including P1-103, PP242, PP30 and Torin 1, and the like.

Non-steroidal anti-inflammatory drugs include Amigesic™ (salsalate), Dolobid™ (diflunisal), Motrin™ (ibuprofen), Orudis™ (ketoprofen), Relafen™ (nabumetone), Feldene™ (piroxicam), ibuprofen cream, Aleve™ and Naprosyn™ (naproxen), Voltaren™ (diclofenac), Indocin™ (indomethacin), Clinoril™ (sulindac), Tolectin™ (tolmetin), Lodine™ (etodolac), Toradol™ (ketorolac), Daypro™ (oxaprozin) and the like.

PDGFR inhibitors include CP-673451, CP-868596 and the like.

Platinum chemotherapeutics include cisplatin, Eloxatin™ (oxaliplatin), eptaplatin, lobaplatin, nedaplatin, Paraplatin™ (carboplatin), picoplatin, satraplatin and the like.

Polo-like kinase inhibitors include BI-2536 and the like.

Phosphoinositide-3 kinase inhibitors include wortmannin, LY-294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include Avastin™ (bevacizumab), ABT-869, AEE-788, Angiozyme™ (a ribozyme that inhibits angiogenesis (Ribozyme Pharmaceuticals (Boulder, Colo.) and Chiron (Emeryville, Calif.)), axitinib (AG-13736), AZD-2171, CP-547632, IM-862, Macugen™ (pegaptanib), Nexavar™ (sorafenib, BAY43-9006), pazopanib (GW-786034), vatalanib (PTK-787 or ZK-222584), Sutent™ (sunitinib or SU-11248), VEGF trap, Zactima™ (vandetanib or ZD-6474) and the like.

Antibiotics include intercalating antibiotics such as aclarubicin, actinomycin D, amrubicin, annamycin, Adriamycin™ (doxorubicin), Blenoxane™ (bleomycin), daunorubicin, Caelyx™ and Myocet™ (liposomal doxorubicin), elsamitrucin, epirubicin, glarubicin, idarubicin, mitorrycin C, nemorubicin, neocarzinostatin, peplomycin, pirarubicin, rebeccamycin, stimalamer, streptozocin, Valstar™ (valrubicin), zinostatin and the like.

Topoisomerase inhibitors include aclarubicin, 9-aminocamptothecin, amonafide, amsacrine, becatecarin, belotecan, BN-80915, Camptosar™ (irinotecan hydrochloride), camptothecin, Cardioxane™ (dexrazoxane), diflomotecan, edotecarin, Ellence™ and Pharmorubicin™ (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include Avastin™ (bevacizumab), CD40-specific antibodies, chTNT-1/B, denosumab, Erbitux™ (cetuximab), Humax-CD4™ (zanolimumab), IGF 1R-specific antibodies, lintuzumab, Panorex™ (edrecolomab), Rencarex™ (WX G250), Rituxan™ (rituximab), ticilimumab, trastuzumab, CD20 antibodies types I and II and the like.

Hormonal therapies include Arimidex™ (anastrozole), Aromasin™ (exemestane), arzoxifene, Casodex™ (bicalutamide), Cetrotide™ (cetrorelix), degarelix, deslorelin, Desopan™ (trilostane), dexamethasone, Drogenil™ (flutamide), Evista™ (raloxifene), Afema™ (fadrozole), Fareston™ (toremifene), Faslodex™ (fulvestrant), Femara™ (letrozole), formestane, glucocorticoids, Hectorol™ (doxercalciferol), Renagel™ (sevelamer carbonate), lasofoxifene, leuprolide acetate, Megace™ (megestrol), Mifeprex™ (mifepristone), Nilandron™ (nilutamide), tamoxifen including Nolvadex™ (tamoxifen citrate), Plenaxis™ (abarelix), prednisone, Propecia™ (finasteride), rilostane, Suprefact™ (buserelin), luteinizing hormone releasing hormone (LHRH) including Trelstar™ (triptorelin), histrelin including Vantas™ (histrelin implant), Modrastane™ (trilostane), Zoladex™ (goserelin) and the like.

Deltoids and retinoids include seocalcitol (EB1089 or CB1093), lexacalcitol (KH1060), fenretinide, Panretin™ (alitretinoin), tretinoin including Atragen™ (liposomal tretinoin), Targretin™ (bexarotene), LGD-1550 and the like.

PARP inhibitors include ABT-888, olaparib, KU-59436, AZD-2281, AG-014699, BSI-201, BGP-15, INO-1001, ONO-2231 and the like.

Plant alkaloids include vincristine, vinblastine, vindesine, vinorelbine and the like.

Proteasome inhibitors include Velcade™ (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, Actimmune™ (interferon gamma-1b), interferon gamma-n1, combinations thereof and the like. Other agents include Alfaferone (IFN-α), BAM-002 (oxidized glutathione), Beromun™ (tasonermin), Bexxar™ (tositumomab), Campath™ (alemtuzumab), CTLA4 (cytotoxic lymphocyte antigen 4), dacarbazine, denileukin, epratuzumab, Granocyte™ (lenograstim), lentinan, leukocyte alpha interferon, imiquimod, MDX-010 (anti-CTLA-4), melanoma vaccine, mitumomab, molgramostim, Mylotarg™ (gemtuzumab ozogamicin), Neupogen™ (filgrastim), OncoVAC-CL, Ovarex™ (oregovomab), pemtumomab (Y-muHMFG1), Provenge™ (sipuleucel-T), sargaramostim, sizofiran, teceleukin, Theracys™ (BCG or Bacillus Calmette-Guerin), ubenimex, Virulizin™ (immunotherapeutic, Lorus Pharmaceuticals), Z-100 (Specific Substance of Maruyama or SSM), WF-10 (tetrachlorodecaoxide or TCDO), Proleukin™ (aldesleukin), Zadaxin™ (thymalfasin), Zenapax™ (daclizumab), Zevalin™ (90Y-ibritumomab tiuxetan) and the like.

Biological response modifiers are agents that modify defense mechanisms of living organisms or biological responses, such as survival, growth or differentiation of tissue cells to direct them to have anti-tumor activity, and include krestin, lentinan, sizofiran, picibanil, PF-3512676 (CpG-8954), ubenimex and the like.

Pyrimidine analogs include cytarabine (cytosine arabinoside, ara C or arabinoside C), doxifluridine, Fludara™ (fludarabine), 5-FU (5-fluorouracil), floxuridine, Gemzar™ (gemcitabine), Tomudex™ (raltitrexed), triacetyluridine, Troxatyl™ (troxacitabine) and the like.

Purine analogs include Lanvis™ (thioguanine), Purinethol™ (mercaptopurine) and the like.

Antimitotic agents include batabulin, epothilone D (KOS-862), N-(2-((4-hydroxy-phenyl)amino)pyridin-3-yl)-4-methoxybenzenesulfonamide, ixabepilone (BMS-247550), paclitaxel, Taxotere™ (docetaxel), larotaxel (PN U-100940, RPR-109881 or XRP-9881), patupilone, vinflunine, ZK-EPO (synthetic epothilone) and the like.

Ubiquitin ligase inhibitors include MDM2 inhibitors such as nutlins, NEDD8 inhibitors such as MLN4924, and the like.

The combination therapy of this present invention may also be used as radiosensitizers that enhance the efficacy of radiotherapy. Examples of radiotherapy include, but are not limited to, external beam radiotherapy (XBRT), teletherapy, brachytherapy, sealed-source radiotherapy, unsealed-source radiotherapy and the like.

Additionally or alternatively, the combination therapy of the present invention can be administered in combination therapy with one or more antitumor or chemotherapeutic agents selected from Abraxane™ (ABI-007), ABT-100 (farnesyl transferase inhibitor), Advexin™ (Ad5CMV-p53 vaccine or contusugene ladenovec), Altocor™ or Mevacor™ (lovastatin). Ampligen™ (poly(I)-poly(C12U), a synthetic RNA), Aptosyn™ (exisulind), Aredia™ (pamidronic acid), arglabin, L-asparaginase, atamestane (1-methyl-3,17-dione-androsta-1,4-diene), Avage™ (tazarotene), AVE-8062 (combretastatin derivative), BEC2 (mitumomab), cachectin or cachexin (tumor necrosis factor), Canvaxin™ (melanoma vaccine), CeaVac™ (cancer vaccine), Celeuk™ (celmoleukin), histamine including Ceplene™ (histamine dihydrochloride), Cervarix™ (AS04 adjuvant-adsorbed human papilloma virus (HPV) vaccine), CHOP (Cytoxan™ (cyclophosphamide)+Adriamycin™ (doxorubicin)+Oncovin™ (vincristine)+prednisone), combretastatin A4P, Cypat™ (cyproterone), DAB(389)EGF (catalytic and translocation domains of diphtheria toxin fused via a His-Ala linker to human epidermal growth factor), dacarbazine, dactinomycin, Dimericine™ (T4N5 liposome lotion), 5,6-dimethylxanthenone-4-acetic acid (DMXAA), discodermolide, DX-895 If (exatecan mesylate), eniluracil (ethynyluracil), squalamine including Evizon™ (squalamine lactate), enzastaurin, EPO-906 (epothilone B), Gardasil™ (quadrivalent human papilloma virus (Types 6, 11, 16, 18) recombinant vaccine), Gastrimmune™, Genasenser™ (oblimersen), GMK (ganglioside conjugate vaccine), GVAX™ (prostate cancer vaccine), halofuginone, histerelin, hdroxycarbamide, ibandronic acid, IGN-101, IL-13-PE38, IL-13-PE38QQR (cintredekin besudotox), IL-13-pseudomonas exotoxin, interferon-α, interferon-γ, Junovan™ and Mepact™ (mifamurtide), lonafarnib, 5,10-methylenetetrahydrofolate, miltefosine (hexadecylphosphocholine), Neovastat™ (AE-941), Neutrexin™ (trimetrexate glucuronate), Nipent™ (pentostatin), Onconase™ (ranpimase, a ribonuclease enzyme), Oncophage™ (vitespen, melanoma vaccine treatment), OncoVAX™ (IL-2 vaccine), Orathecin™ (rubitecan), Osidem™ (antibody-based cell drug), Ovarex™ MAb (murine monoclonal antibody), paclitaxel albumin-stabilized nanoparticle, paclitaxel, Pandimex™ (aglycone saponins from ginseng comprising 20(S)-protopanaxadiol (aPPD) and 20(S)-protopanaxatriol (aPPT)), panitumumab, Panvac™-VF (investigational cancer vaccine), pegaspargase, peginterferon alfa (PEG interferon A), phenoxodiol, procarbazine, rebimastat, Removab™ (catumaxomab), Revlimid™ (lenalidomide), RSR13 (efaproxiral), Somatuline™ LA (lanreotide), Soriatane™ (acitretin), staurosporine (Streptomyces staurospores), talabostat (PT100), Targretin™ (bexarotene), Taxoprexin™ (docosahexaenoic acid (DHA)+paclitaxel), Telcyta™ (canfosfamide, TLK-286), Temodar™ (temozolomide), tesmilifene, tetrandrine, thalidomide, Theratope™ (STn-KLH vaccine), Thymitaq™ (nolatrexed dihydrochloride), TNFerade™ (adenovector: DNA carrier containing the gene for tumor necrosis factor-α), Tracleer™ or Zavesca™ (bosentan), TransMID-107R™ (KSB-311, diphtheria toxins), tretinoin (retin-A), Trisenox™ (arsenic trioxide), Ukrain™ (derivative of alkaloids from the greater celandine plant), Virulizin™, Vitaxin™ (anti-αvβ3 antibody), Xcvtrin™ (motexafin gadolinium), Xinlay™ (atrasentan), Xyotax™ (paclitaxel poliglumex), Yondelis™ (trabectedin), ZD-6126 (N-acetylcolchinol-O-phosphate), Zinecard™ (dexrazoxane), zoledronic acid, zorubicin and the like.

Other objects and features will be in part apparent and in part pointed out hereinafter.

EXAMPLES

The following non-limiting examples are provided to further illustrate the present invention.

Figure 2A:
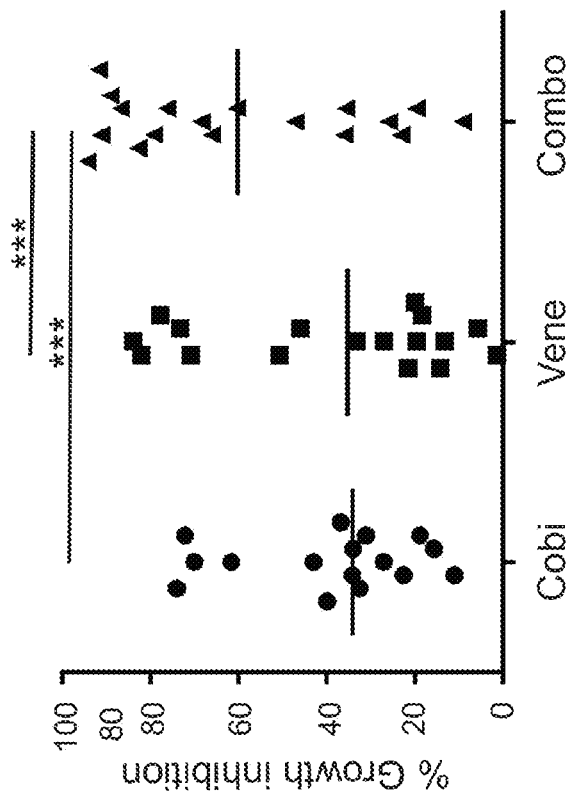
FIGS. 2A, 2B, and 2C. Anti-leukemia activities of cobimetinib/venetoclax against primary AML blasts.
Figure 2A:
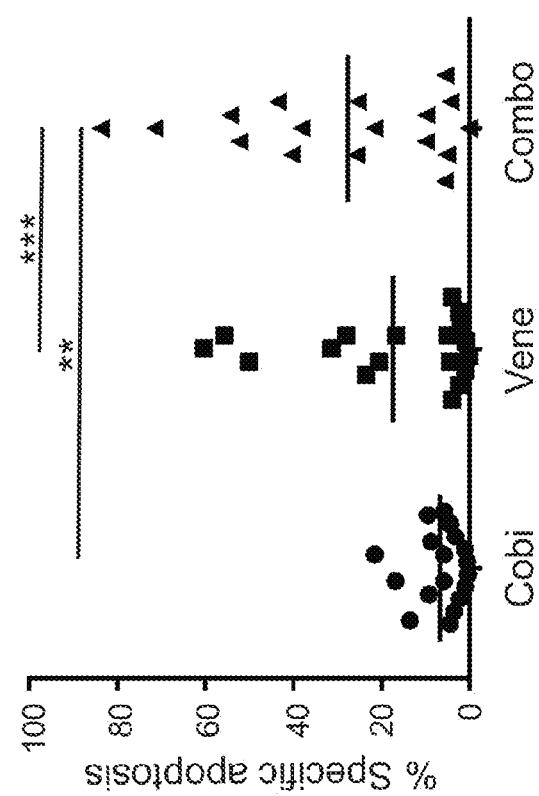
Figure 2B:
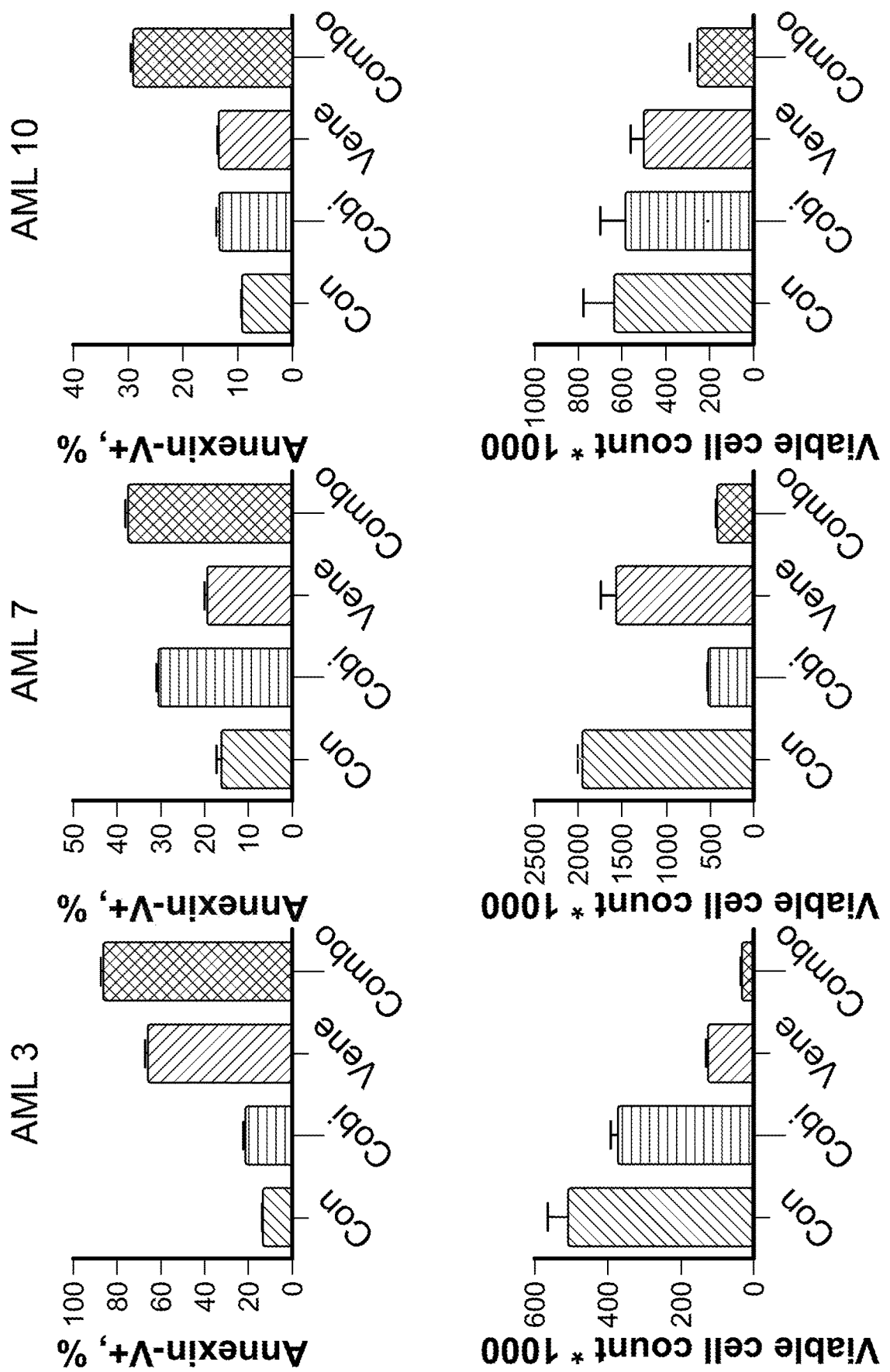
Figure 2C:
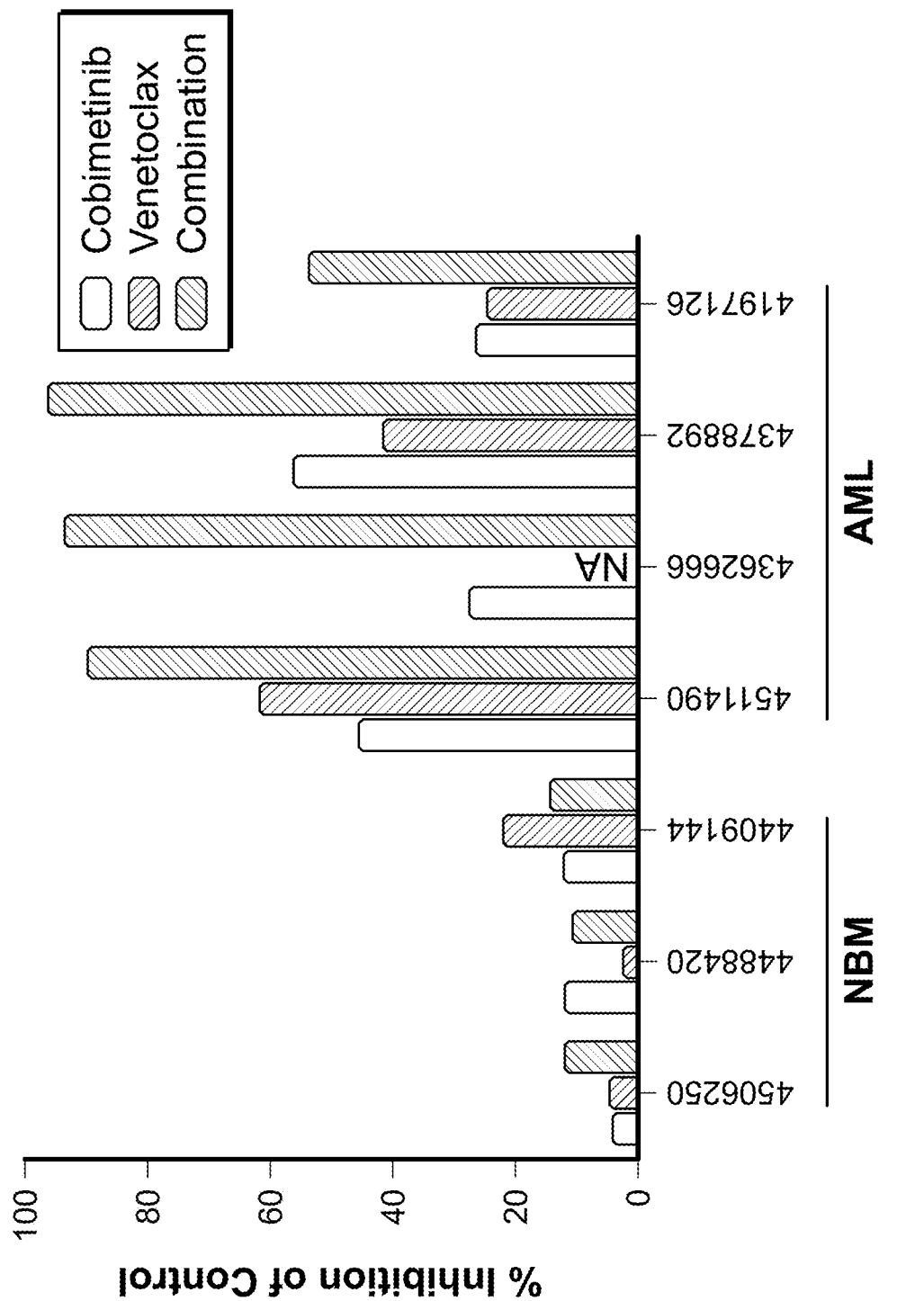

The activity of 4-(4-{[2-(4-chlorophenyl)-4,4-dimethyl-cyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide (ABT-199, or venetoclax) and [3,4-Difluoro-2-(2-fluoro-4-iodoanilino)phenyl]{3-hydroxy-3-[(2S)-piperidin-2-yl]azetidin-1-yl}methanone (cobimetinib) was examined in a panel of myeloid leukemia cell lines with diverse genetic alterations. The $IC_{50}$ values of cobimetinib ranged from <0.01 μM to >1 μM after 72 hours of drug treatment but did not correlate with the basal level of p-ERK1/2. (FIG. 1A). In 7 out of 11 cell lines, combination of the agents elicited synergistic growth inhibition. Notably synergism of venetoclax with cobimetinib was observed in venetoclax-resistant cell lines (MOLM14, OCI-AML3, NB4 and THP1). (FIGS. 1B through 1L). In a long-term culture of primary AML blasts, the combination of venetoclax and cobimetinib predominantly suppressed cell proliferation and induced distinct apoptotic cell death in a subset of AML samples. The clonogenic potential of myeloid progenitors was significantly suppressed by the combination, while the normal progenitor function was minimally affected. (FIGS. 2A, 2B, and 2C).

Ongoing analysis of pharmacodynamic markers include transcriptome assessment by RNA sequencing, functional proteomics by reverse phase protein array (RPPA), and quantification of Bcl-2:BIM and MCL-1:BIM complexes using the electrochemiluminescent ELISA assay (Meso Scale Discovery, MSD-ELISA). RPPA is a high-throughput technology that performs protein assays on thousands of samples simultaneously. This protein array platform measures levels of protein expression, as well as protein modifications such as phosphorylation. RPPA data demonstrated differentially expressed proteins in sensitive and resistant cell lines to cobimetinib or venetoclax as single agents or in combination. See the following Tables 1, 2, and 3.

TABLE 1

COBIMETINIB: SENSITIVE V. RESISTANT

| Protein | Pval | Mean. Res | Mean. Sens |
|---|---|---|---|
| Bax | 8.64E−15 | 1.010 | 1.307 |
| Bim | 2.87E−13 | 0.893 | 1.175 |
| ERK 1/2 (T202/Y204) | 1.47E−09 | 1.073 | 1.988 |
| FLT3 (Y589/591) | 1.71E−12 | 0.948 | 1.256 |
| p16INK4a | 6.56E−23 | 2.220 | 1.184 |
| p38MAP (T180/Y182) | 0.00174 | 0.983 | 1.275 |
| p53 | 4.87E−10 | 0.939 | 1.373 |
| PTEN | 3.92E−18 | 1.013 | 1.361 |
| PTEN (S380) | 0.0003 | 1.049 | 1.335 |
| RSK3 (T356/S360) | 1.09E−15 | 0.859 | 1.495 |
| S6 (S235/236) | 0.00012 | 0.748 | 1.174 |

TABLE 2

VENETOCLAX: SENSITIVE V. RESISTANT

| Protein | Pval | Mean. Res | Mean. Sens |
|---|---|---|---|
| bRaf (T401) | 5.44E−10 | 1.263 | 0.927 |
| Bax | 1.48E−15 | 0.958 | 1.227 |
| Bcl-2 | 1.28E−19 | 0.817 | 1.081 |
| Bim | 3.41E−20 | 1.143 | 0.811 |
| p16INK4a | 3.09E−06 | 1.989 | 1.593 |
| PTEN | 2.39E−20 | 0.704 | 1.495 |
| PTEN (S380) | 1.88E−09 | 0.839 | 1.369 |
| S6 (S240/244) | 8.51E−05 | 1.918 | 1.571 |

TABLE 3

COMBINATION: SENSITIVE V. RESISTANT

| Protein | Pval | Mean. Res | Mean. Sens |
|---|---|---|---|
| Bad | 1.65E−07 | 1.232 | 0.923 |
| Bad (S112) | 3.26E−07 | 1.272 | 0.938 |
| Bcl2 | 2.12E−22 | 0.373 | 1.051 |
| Caspase 3 | 2.66E−16 | 1.526 | 0.998 |
| Caspase 3 Cleaved D175 | 0.000127321 | 0.938 | 1.359 |
| Caspase 7 Cleaved D198 | 5.53E−09 | 0.590 | 1.771 |
| Caspase 8 Cleaved D391 | 2.19E−05 | 0.804 | 1.409 |
| eIF2a (S51) | 2.26E−08 | 1.393 | 0.850 |
| ERK 1/2 | 9.81E−13 | 0.802 | 1.098 |
| p16INK4a | 1.03E−14 | 3.786 | 1.326 |
| p70 p85 S6 (S371/S394) | 1.84E−05 | 0.726 | 1.054 |
| PARP Cleaved D214 | 9.37E−07 | 0.680 | 1.477 |
| PTEN | 2.39E−11 | 0.508 | 1.178 |
| PTEN (S380) | 9.64E−05 | 0.661 | 1.109 |
| RSK3 (T356/S360) | 8.80E−06 | 0.789 | 1.130 |

Figure 3A:
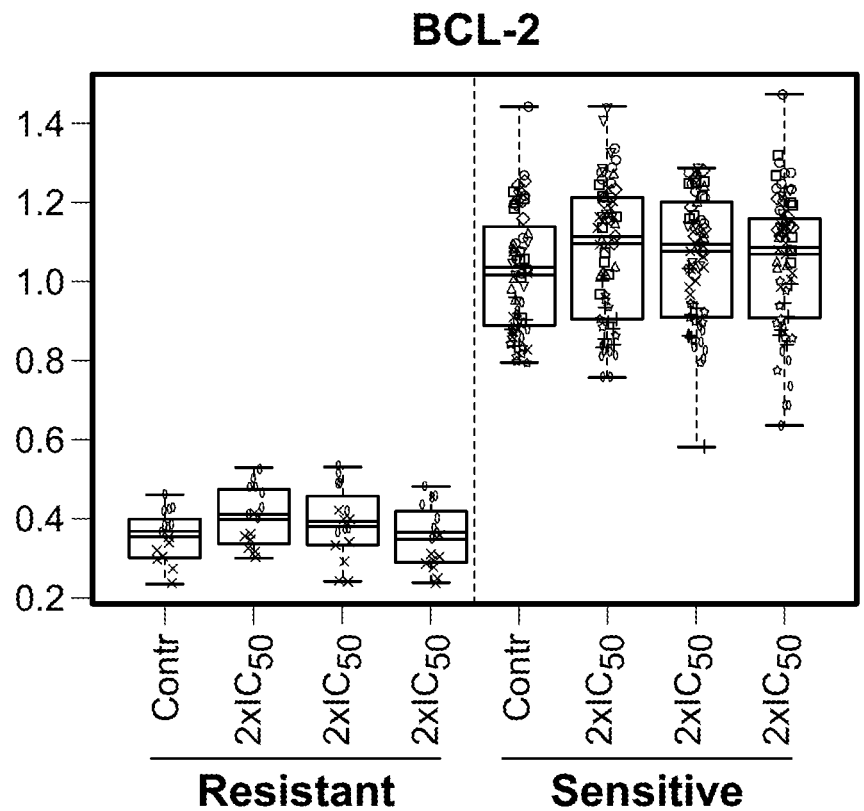
FIGS. 3A, 3B, 3C, 3D, and 3E demonstrate a Pharmacodynamic study of underlying mechanisms of cobimetinib/venetoclax combination.
Figure 3B:
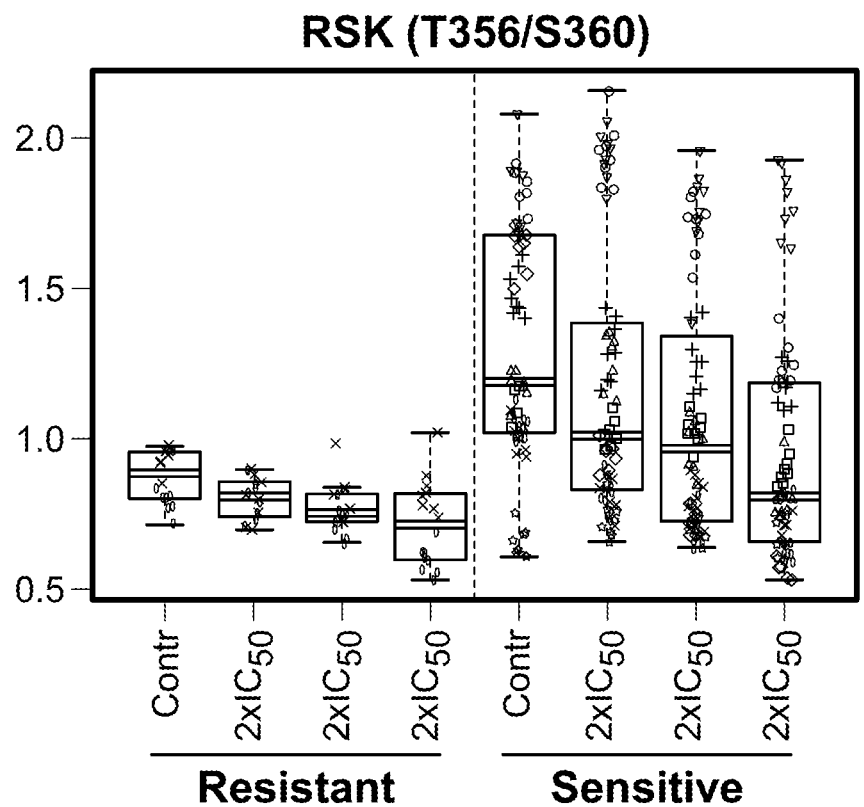
Figure 3C:
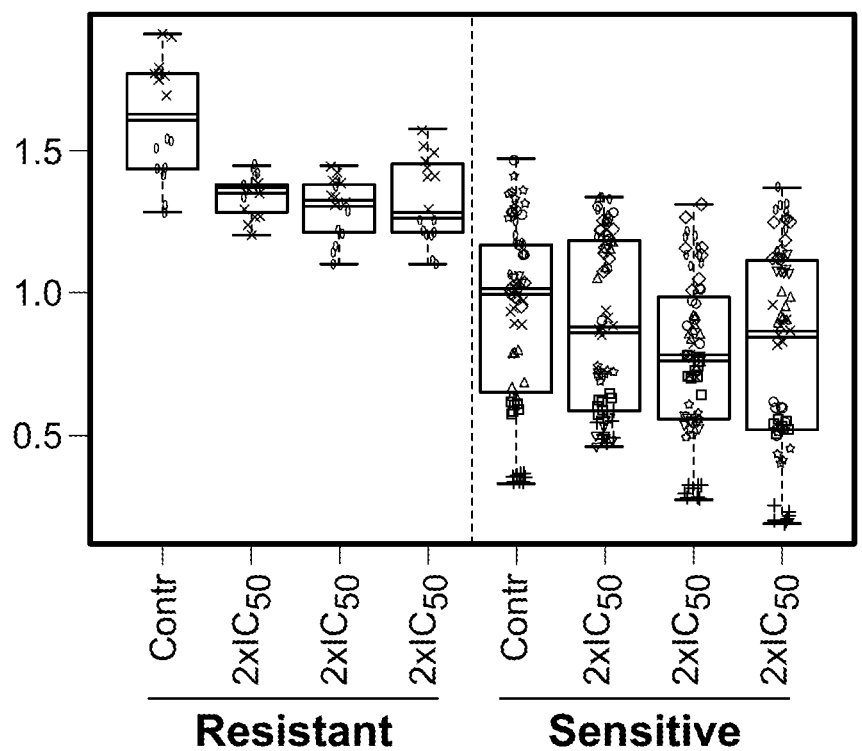
Figure 3D:
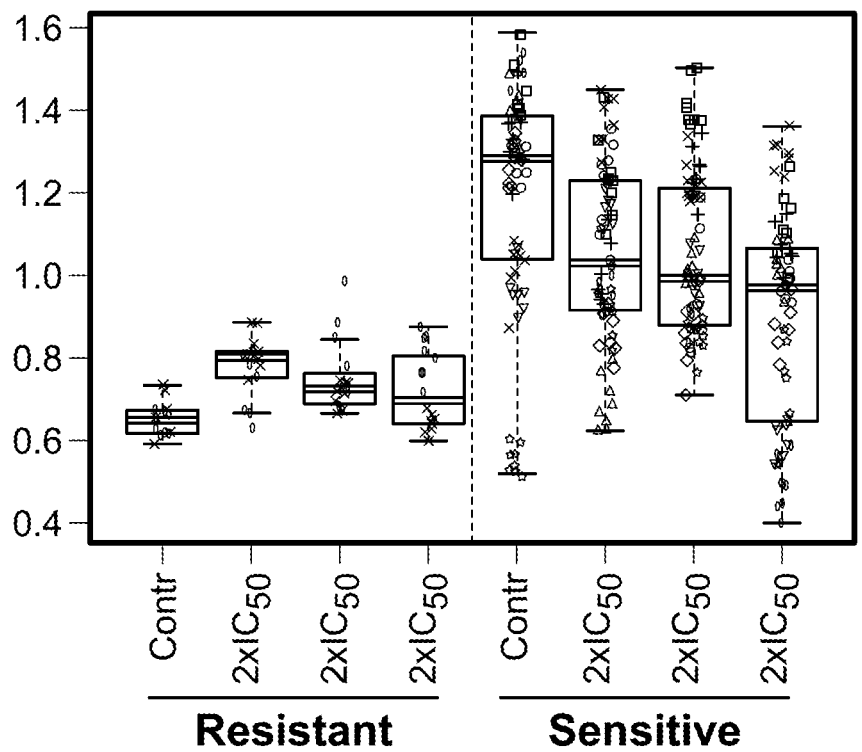
Figure 3E:
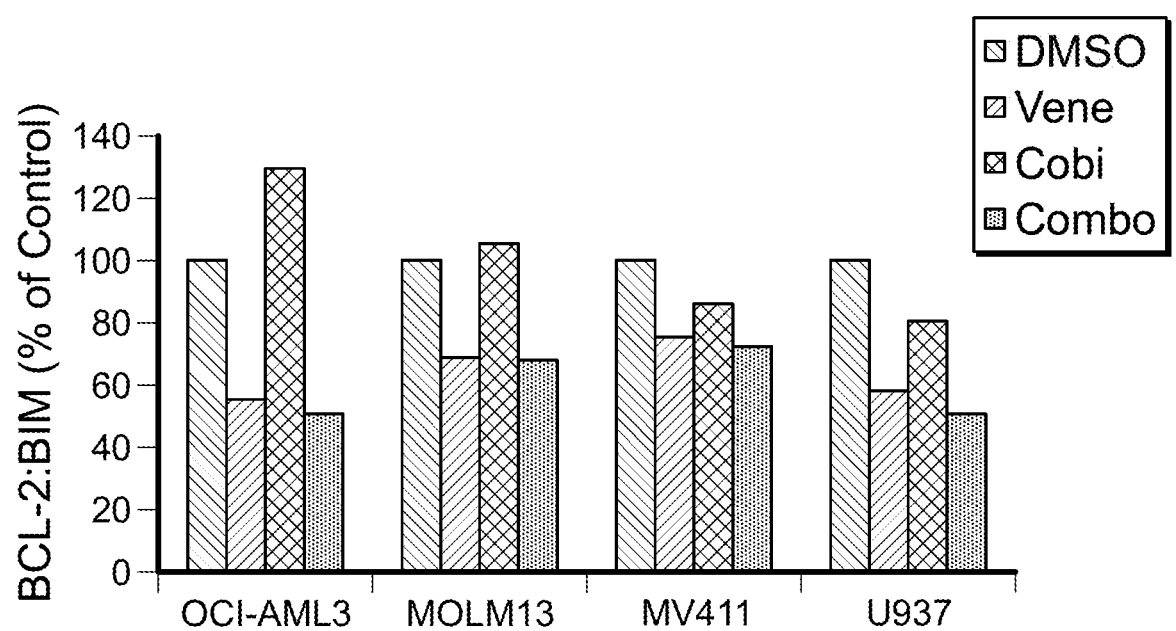

Representative proteins that are differentially expressed in sensitive and resistant cell lines to the combination. (FIGS. 3A, 3B, 3C, and 3D). The preliminary MSD data revealed that Bcl-2:BIM complex was disrupted by venetoclax in most cell lines and accumulated following cobimetinib treatment in OCI-AML3 cells, which may be due to the disruption of MCL-1:BIM complex by inhibition of MEK, releasing BIM to bind with Bcl-2. (FIG. 3E).

Figure 4A:
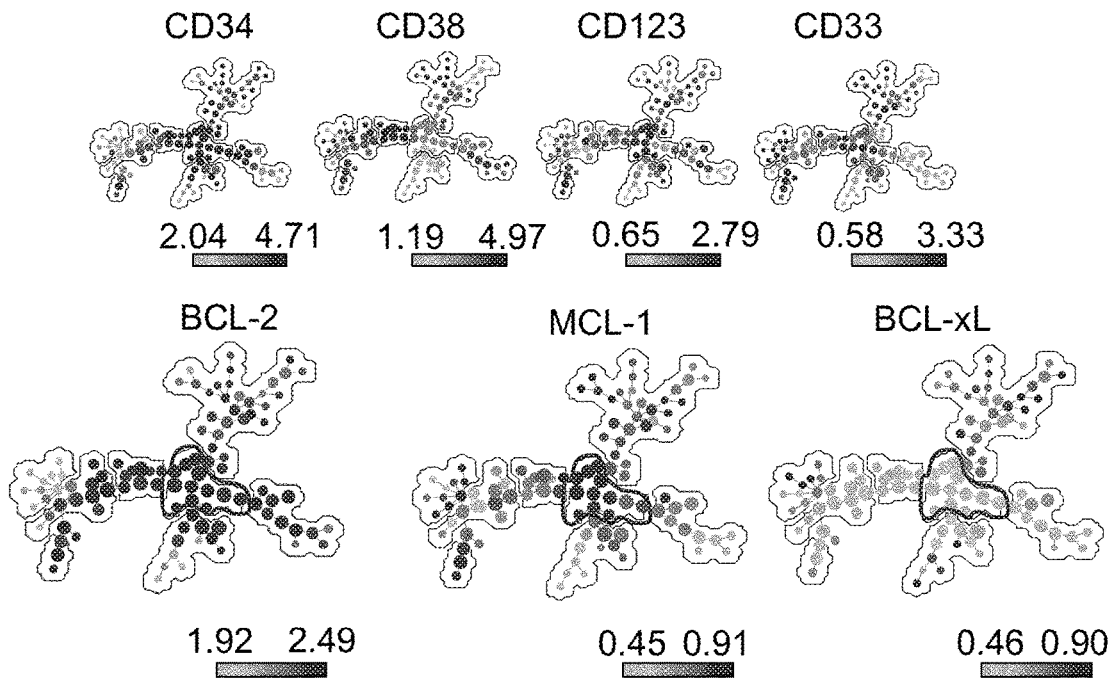
Figure 4A:
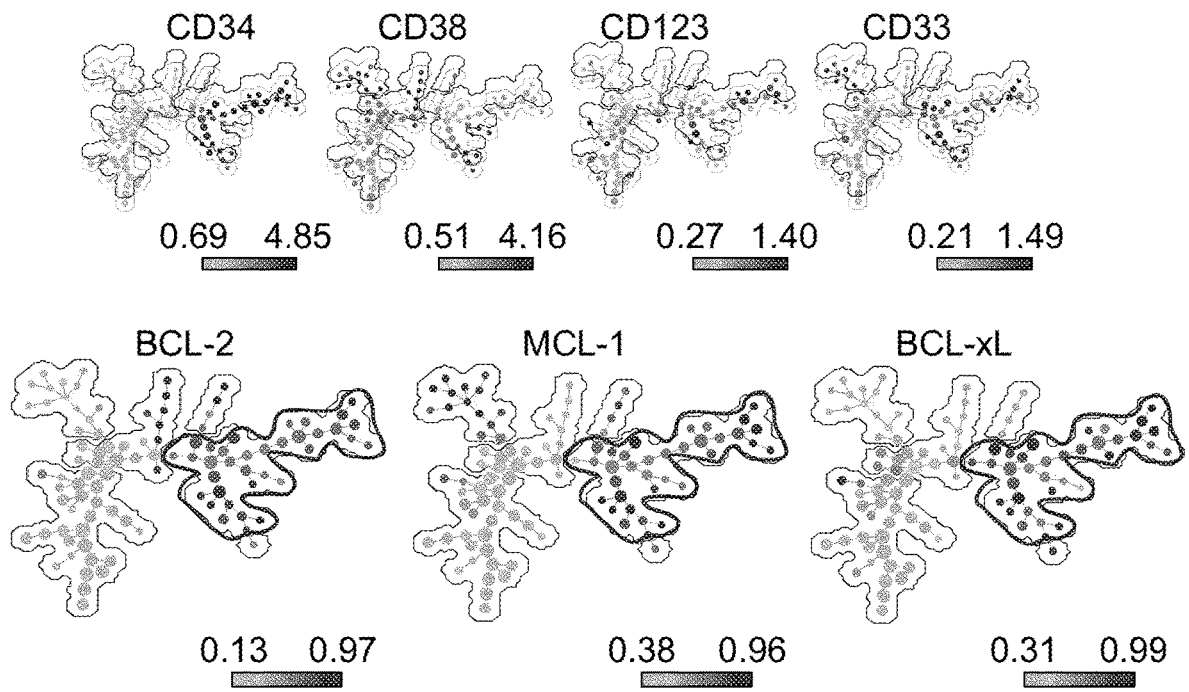
Figure 5A:
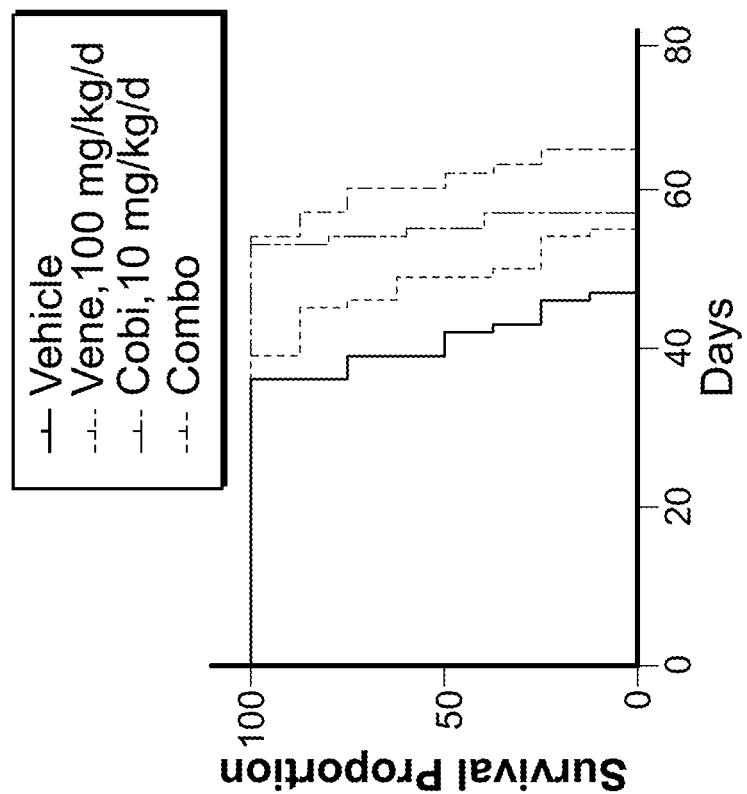
FIGS. 5A, 5B, 5C, 5D, and 5E demonstrate Anti-leukemia efficacy of cobimetinib and venetoclax in OCI-AML3 and MOLM13 AML model in vivo. OCI-AML3/Luc/GFP cells ($1\times10^6$ per mouse) were injected intravenously into NSG mice.
Figure 5B:
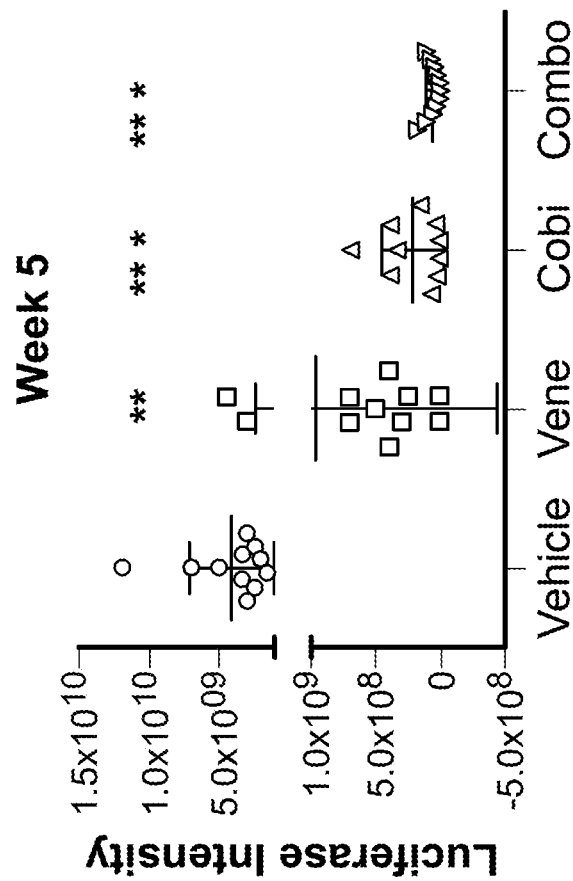
Figure 5C:
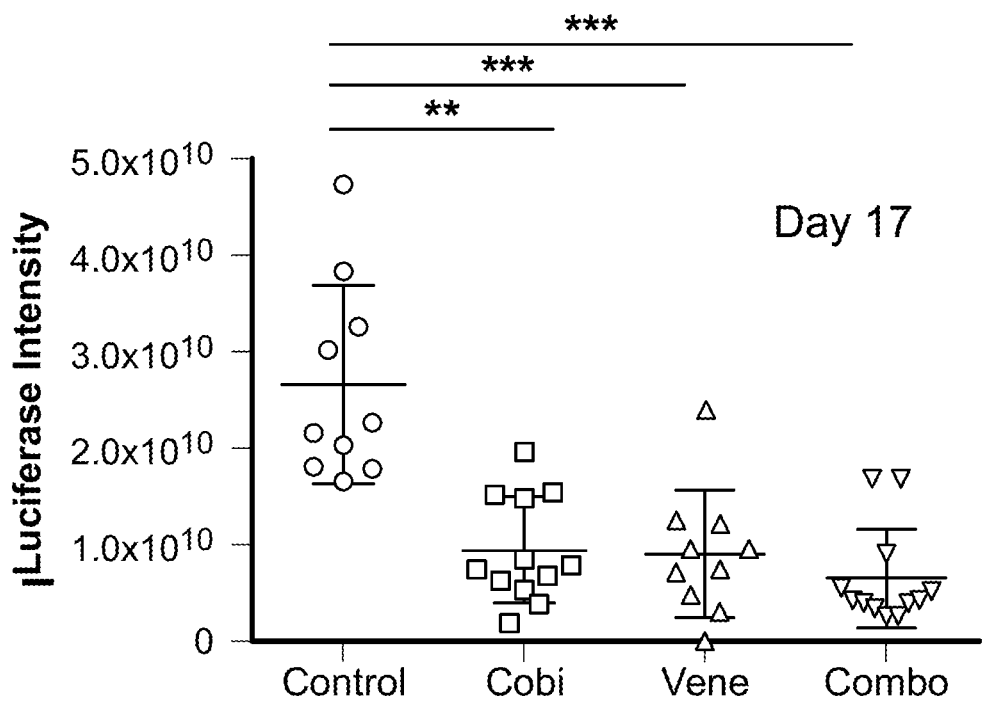
Figure 5D:
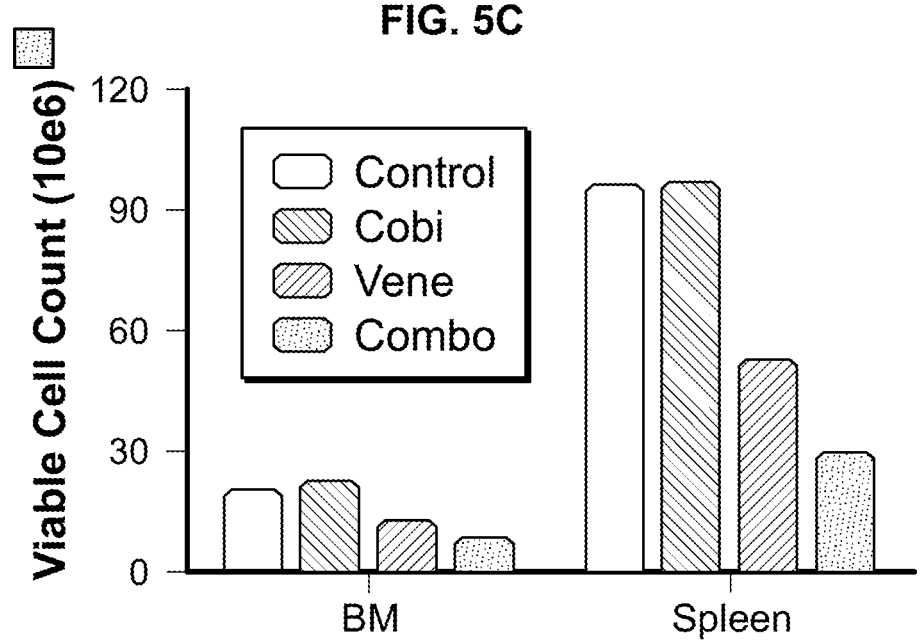
Figure 5E:
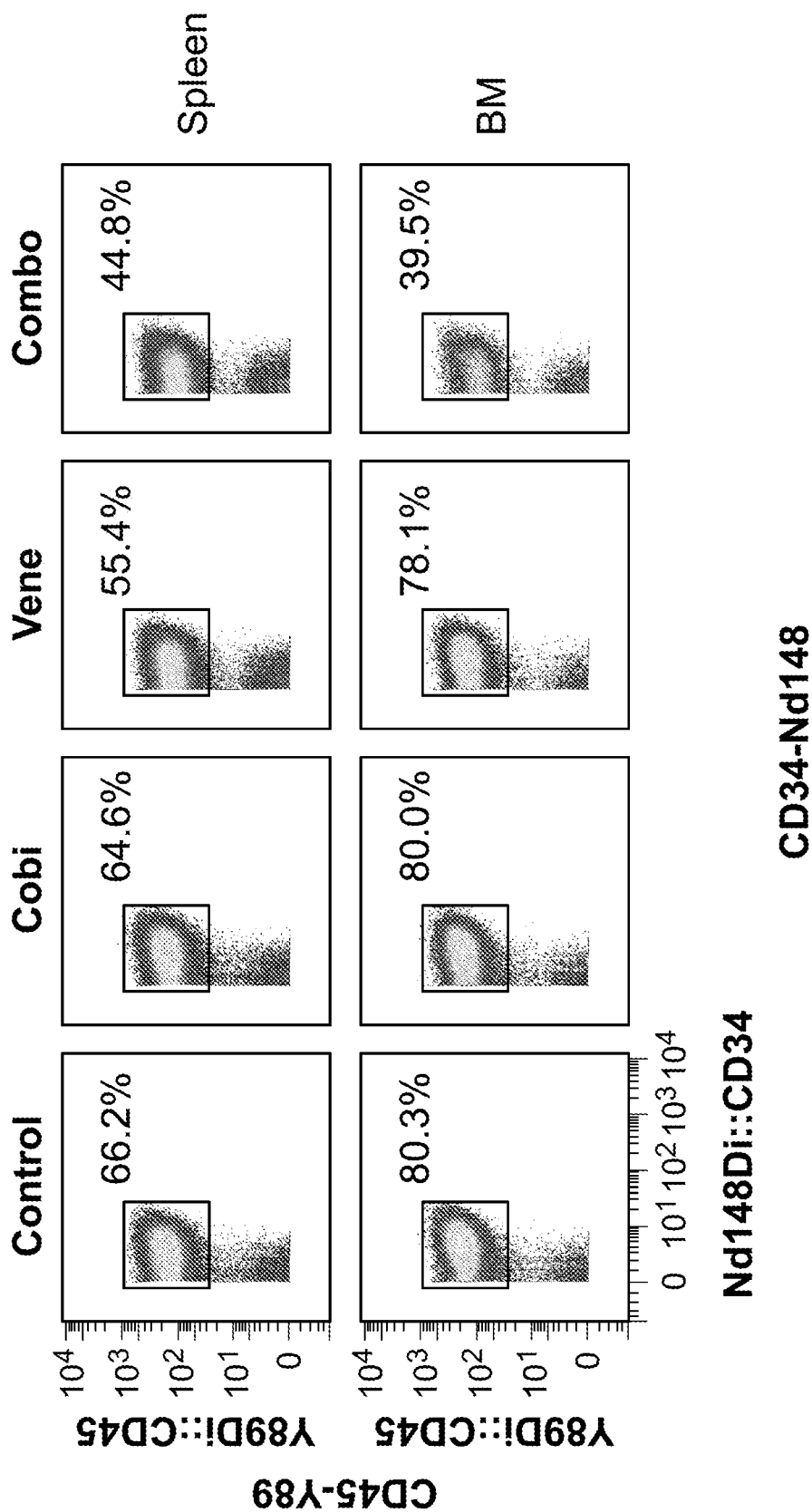

We next investigated signaling patterns and Bcl-2 family protein expression in AML stem/progenitor cells using a 34-antibody panel and time-of-flight mass cytometry (CyTOF). CyTOF is a variation of flow cytometry in which antibodies are labeled with heavy metal ion tags rather than fluorochromes. Readout is by time-of-flight mass spectrometry. This allows for the combination of many more antibody specificities in single samples, without significant spillover between channels. In AML 4295468, Bcl-2 was expressed in leukemia blasts, with enrichment in a progenitor AML population phenotypically defined as CD45dimCD34+CD38+CD123+CD33+. (FIG. 4A). The high expression level of Bcl-2 and low expression of MCL-1 and BCL-XL may account for sensitivity to venetoclax in AML 4295468. A venetoclax-resistant AML (4366894) showed low expression of Bcl-2 in CD45dimCD34+CD38-CD123+CD33+ population. (FIG. 4B). In AML 4295468, both basal and G-CSF- or SCF-stimulated p-ERK was efficiently downregulated by cobimetinib; however, G-CSF-evoked p-STAT3/5 and SCF-induced p-AKT were only slightly reduced. (FIG. 4C). Notably we observed increased phosphorylation of STAT5 pathway upon treatment with cobimetinib, suggesting that active MAPK signals inhibit phosphorylation of the JAK-STAT pathway, as previously reported (Krasilnikov et al. Oncogene, 2003 and Lee at al. Cancer Cell, 2014). In AML 4366894, p-ERK was also reduced, however, G-CSF-induced p-STAT3/5 were not significantly changed. To test the efficacy of both compounds in vivo, we injected NSG mice with genetically engineered OCI-AML3/Luc/GFP cells. Bioluminescent imaging (BLI) demonstrated significantly reduced leukemia burden in treated groups compared to controls, more prominently in the cobimetinib single agent and venetoclax plus cobimetinib co-treated mice. (FIGS. 5A and 5B). To further explore the anti-leukemia efficacy of both compounds, we injected NSGS mice with genetically engineered MOLM3/Luc/GFP cells. Bioluminescent imaging demonstrated significantly reduced leukemia burden in treated groups compared to controls, more prominently in the venetoclax group and in venetoclax plus cobimetinib co-treated mice. (FIG. 5C). Human CD45 engraftment and cell counts in both bone marrow and spleen demonstrated a trend towards decreased tumor burden when venetoclax was combined with cobimetinib in vivo. (FIGS. 5D and 5E).

In summary, the data demonstrate that combinatorial blockade of MAPK and Bcl-2 pathways is synergistic in the majority of AML cell lines tested and can overcome intrinsic resistance to venetoclax. Further, cobimetinib/venetoclax combination inhibited proliferation, induced apoptosis and reduced clonogenicity in a subset of primary AML samples, but not in normal hematopoietic precursors. In addition, differentially overexpressed proteins were identified in cell lines sensitive or resistant to either single agents or to cobimetinib/venetoclax combination. MSD assay revealed that venetoclax but not cobimetinib disrupted the Bcl-2:BIM complex. CyTOF mass cytometry enables measurements of intracellular signaling pathways and Bcl-2 family members in antigen-defined AML stem/progenitor cell populations. Finally, the combination of venetoclax and cobimetinib reduces AML tumor burden and extends survival in OCI-AML3 AML model and MOLM13 AML model in vivo.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawings shall be interpreted as illustrative and not in a limiting sense.

What is claimed is:

1. A method of treating a proliferative disorder, the method comprising administering to a mammal in need thereof a therapeutically effective amount of a combination of:
   a MEK inhibitor, wherein the MEK inhibitor is [3,4-difluoro-2-(2-fluoro-4-iodoanilino)phenyl]{3-hydroxy-3-[(2S)-piperidin-2-yl]azetidin-1-yl}methanone (cobimetinib) or a pharmaceutically acceptable salt thereof; and
   a selective Bcl-2 inhibitor, wherein the selective Bcl-2 inhibitor is 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide (ABT-199) or a pharmaceutically acceptable salt thereof;
   wherein the proliferative disorder is a blood cancer.

2. The method of claim 1 wherein the blood cancer is selected from the group consisting of chronic lymphocytic leukemia, acute lymphocytic leukemia, Hodgkin's disease, chronic or acute leukemia, acute myeloid leukemia, chronic myeloid leukemia, lymphocytic lymphoma, lymphoblastic leukemia, follicular lymphoma, multiple myeloma, non-Hodgkin's lymphoma, and combinations thereof.

3. The method of claim 1 wherein the blood cancer is acute myeloid leukemia.

4. The method of claim 1 wherein the blood cancer is multiple myeloma.

5. The method of claim 1 wherein the mammal is a human.

6. The method of claim 1 wherein the MEK inhibitor is administered concurrently with the selective Bcl-2 inhibitor.

7. The method of claim 1 wherein the MEK inhibitor and the selective Bcl-2 inhibitor are co-formulated.

8. The method of claim 7 wherein the MEK inhibitor and the selective Bcl-2 inhibitor are co-formulated in a pharmaceutical composition further comprising a pharmaceutically acceptable excipient.

9. The method of claim 1 wherein the MEK inhibitor is administered sequentially with the selective Bcl-2 inhibitor.

10. The method of claim 9 wherein the MEK inhibitor and the selective Bcl-2 inhibitor are formulated in separate orally available dosage forms.

11. The method of claim 1 wherein the blood cancer is an ABT-199-resistant proliferative disorder.

12. The method of claim 3 wherein the blood cancer is ABT-199-resistant acute myeloid leukemia.

* * * * *